US009468634B2

(12) United States Patent
Ashrafian et al.

(10) Patent No.: US 9,468,634 B2
(45) Date of Patent: *Oct. 18, 2016

(54) TREATMENT OF HEART FAILURE

(71) Applicant: Heart Metabolics Limited, Dublin (IE)

(72) Inventors: Houman Ashrafian, Oxford (GB);
Michael Paul Frenneaux, Norwich (GB)

(73) Assignee: Heart Metabolics Limited, Dublin (IE)

( * ) Notice: Subject to any disclaimer, the term of this patent is extended or adjusted under 35 U.S.C. 154(b) by 290 days.

This patent is subject to a terminal disclaimer.

(21) Appl. No.: 13/839,313

(22) Filed: Mar. 15, 2013

(65) Prior Publication Data
US 2013/0210720 A1 Aug. 15, 2013

Related U.S. Application Data

(63) Continuation of application No. 12/785,077, filed on May 27, 2010, now Pat. No. 8,440,697, which is a continuation of application No. PCT/GB2009/050539, filed on May 20, 2009, and a continuation-in-part of application No. PCT/GB2008/003913, filed on Nov. 24, 2008.

(60) Provisional application No. 60/990,933, filed on Nov. 29, 2007.

(30) Foreign Application Priority Data

Nov. 23, 2007 (GB) .................................. 0723100.4

(51) Int. Cl.
*A61K 31/4458* (2006.01)
*A61K 45/06* (2006.01)

(52) U.S. Cl.
CPC ........... *A61K 31/4458* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,645,776 B2 | 1/2010 | Ackerman et al. |
| 8,440,697 B2 | 5/2013 | Ashrafian et al. |
| 8,470,806 B2 | 6/2013 | Frenneaux |
| 8,697,677 B2 | 4/2014 | Frenneaux |
| 8,697,728 B2 | 4/2014 | Ashrafian et al. |
| 2003/0162824 A1 | 8/2003 | Krul |
| 2005/0203072 A1 | 9/2005 | Rudolph et al. |
| 2007/0275997 A1 | 11/2007 | Frenneaux |
| 2010/0331364 A1 | 12/2010 | Ashrafian et al. |
| 2012/0101128 A1 | 4/2012 | Frenneaux |
| 2012/0122925 A1 | 5/2012 | Ashrafian et al. |
| 2013/0210719 A1 | 8/2013 | Ashrafian et al. |
| 2013/0210720 A1 | 8/2013 | Ashrafian et al. |
| 2013/0331321 A1 | 12/2013 | Frenneaux |
| 2014/0019207 A1 | 1/2014 | Kraus et al. |
| 2014/0065241 A1 | 3/2014 | Sallustio et al. |
| 2014/0194466 A1 | 7/2014 | Ashrafian et al. |

FOREIGN PATENT DOCUMENTS

| | | |
|---|---|---|
| AU | 2012903850 | 9/2012 |
| CN | 1950084 A | 4/2007 |
| JP | 2007-528378 A | 10/2007 |
| WO | 97/00678 | 1/1997 |
| WO | 2005/087233 | 9/2005 |
| WO | 2005/097121 | 10/2005 |
| WO | 2007/096251 | 8/2007 |
| WO | 2009/066085 | 5/2009 |
| WO | 2010/131033 | 11/2010 |
| WO | 2010/133815 | 11/2010 |
| WO | WO-2014/036603 A1 | 3/2014 |
| WO | WO-2015/131231 A1 | 9/2015 |

OTHER PUBLICATIONS

Lee et al. in Circulation 2005;112:3280-3288.*
Cole et al. in Circulation 81(4), 1260-1270 (1990).*
Opherk et al. in Circulation 1981:63:817-825.*
Mayo Clinic CHF Symptoms (http://www.mayoclinic.org/diseases-conditions/heart-failure/basics/symptoms/con-20029801) (retrieved from the internet Nov. 10, 2015).*
Mayo Clinic Angina Symptoms (http://www.mayoclinic.org/diseases-conditions/angina/basics/symptoms/ con-20031194) (retrieved from the internet Nov. 10, 2015).*
Myocardial Protection by Calcium Antagonists, Lionel H. Opie, Ed., pp. 135-136, Author's Publishing House, N.Y. (1994).*
Chatterjee et al. in Journal of Cardiac Failure 13(7) 569-576 (2007).*
Balgi et al., "Screen for Chemical Modulators of Autophagy Reveals Novel Therapeutic Inhibitors of mTORC1 Signaling," PLoS One, 4(9):e7124 (2009).
Beck et al., "Determination of perhexiline and hydroxyperhexiline in plasma by liquid chromatography-mass spectrometry" J Chromatogr B, 805:87-91 (2004).
Ceccarelli et al., "Carnitine Palmitoyltransferase (CPT) Modulators: A Medicinal Chemistry Perspective on 35 Years of Research," J. Med Chem, 54:3109-3152 (2011).
Davies et al., "Clinical inhibition of CYP2D6-catalysed metabolism by the antianginal agent perhexiline" Br J Clin Pharmacol, 57(4):456-463 (2004).
Davies et al., "The influence of CYP2D6 genotype on trough plasma perhexiline and cis-OH-perhexiline concentrations following a standard loading regimen in patients with myocardial ischaemia" Br J Clin Pharmacol, 61(3):321-325 (2006).

(Continued)

*Primary Examiner* — Dennis Heyer
(74) *Attorney, Agent, or Firm* — Clark & Elbing LLP; Kristina Bieker-Brady

(57) ABSTRACT

The invention relates to perhexiline, or a pharmaceutically acceptable salt thereof, for use in the treatment of heart failure, as well as to a method for treating heart failure, which comprises administering to an animal in need thereof an effective amount of perhexiline, or a pharmaceutically acceptable salt thereof, to treat said heart failure. The invention further relates to a treatment programme for treating heart failure, which involves the co-use or co-administration of perhexiline with one or more other compounds that are advantageous in treating heart failure or the symptoms thereof.

13 Claims, 6 Drawing Sheets

(56) References Cited

OTHER PUBLICATIONS

Eason et al., "The Importance of Pharmacokinetic and Receptor Studies in Drug Safety Evaluation," Regulatory Toxicology and Pharmacology, 11:288-307 (1990).
International Search Report and Written Opinion dated Nov. 6, 2013, issued in PCT/AU2013/001008.
International-Type Search dated Mar. 18, 2013 issued in AU2012903850.
Kitoh H. et al., "Perhexiline maleate in the treatment of fibrodysplasia ossificans progressiva: an open-labeled clinical trial," Orphanet Journal of Rare Diseases, 8:163 (2013).
Licari et al., "The effects of (+)- and (−)-enantiomers of Perhexiline on HepG2 cell growth," The 3rd Australian Health & Medical Research Congress, p. 419 (abstract #1373) (2006).
Licari J. et al., "The Effect of the Enantiomers of Perhexiline on Neutrophil Superoxide Formation," 4th Australian Heath and Medical Research Congress, p. 352 (abstract #661) (2008).
Ling L. et al., "Effects of Aging, Renal Dysfunction, Left Ventricular Systolic Impairment, and Weight on Steady State Pharmacokinetics of Perhexiline," Ther Drug Monit, 33:251-256 (2011).
Morris et al., "Application of an Improved HPLC Perhexiline Assay to Human Plasma Specimens," J. Liq. Chromatogr., 15(18):3219-3232 (1992).
Morrow D. et al., "Modulation of Myocardial Energetics: Emerging Evidence for a Therapeutic Target in Cardiovascular Disease", Circulation, 112(21):3218-3221 (2005).
National Heart Foundation of Australia and the Cardiac Society of Australia and new Zealand (Chronic Heart Failure Guidelines Expert Writing Panel). Guidelines for the prevention, detection and management of chronic heart failure in Australia. Updated Oct. 2011.
Nobuhara, M. et al., "Mitochondrial dysfunction caused by saturated fatty acid loading induces myocardial insulin-resistance in differentiated H9c2 myocytes: a novel ex vivo myocardial insulin-resistance model," Exp Cell Res, 319:955-66 (2013).
Oates et al., "The metabolic disposition of the stereoisomers of perhexiline maleate and the influence of oxidation phenotype," Proceedings of the BPS, 307P (abstract) (1984).
Otsuka et al. "Echocardiographic evaluation of ventricular systolic and diastolic function in heart failure," Journal of Clinical and Experimental Medicine, 216(1):99-104 (2006).
Pogatsa G.,"Metabolic energy metabolism in diabetes: therapeutic implications," Coronary Artery Disease, 12(Suppl 1):529-533 (2001).
Sallustio B.C. "Monitoring perhexiline therapy." Perhexiline Progress, Issue 2:1-4 (1998).
Sallustio B.C. and Morris R.G., "Assessment of Interlaboratory Performance in the Provision of Perhexiline Therapeutic Drug Monitoring Services in Australia," Ther. Drug Monit., 21:389-394 (1999).
Therapeutic Goods Administration Product Information for PEXSIG, Sep. 2011.
Yamamoto, et al., "Heart Failure with Preserved Ejection Fraction—What is Known and Unknown," Circulation Journal, 73:404-410 (2009).
Butera et al., "Heart Rate Variability in Children With Hypertrophic Cardiomyopathy", Heart, 89:205-206 (2003).
Maron et al., "Usefulness of B-Type Natriuretic Peptide Assay in the Assessment of Symptomatic State in Hypertrophic Cardiomyopathy:", Circulation, 109:984-989 (2004).
Ashrafian et al., "Perhexiline," Cardiovascular Drug Reviews, 25(2):76-97 (2007).
Williams et al., "Syncope in hypertrophic cardiomyopathy: mechanisms and consequences for treatment," Europace, 9:817-822 (2007).
Drexler et al., "Explaining Fatigue in Congestive Heart Failure," Annu. Rev. Med., 47:241-256 (1996).
Jerant et al., "Reducing the Cost of Frequent Hospital Admissions for Congestive Heart Failure: A Randomized Trial of a Home Telecare Intervention," Medical Care, 39(11):1234-1245 (2001).
Krum, "Guidelines for management of patients with chronic heart failure in Australia," The Medical Journal of Australia, 174(9):459-466 (2001).
Gould et al., "Stereoselective pharmacokinetics of perhexiline," Xenobiotica, 16(5):491-502 (1986).
Hunt et al., "ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure)" Circulation, 104:2996-3007 (2001).
Sasson et al., "Causal Relation Between the Pressure Gradient and Left Ventricular Ejection Time in Hypertrophic Cardiomyopathy," JACC, 13:1275-1279 (1989).
De Keulenaer et al., "Systolic and diastolic heart failure: Different phenotypes of the same disease?" European Journal of Heart Failure, 9:136-143 (2007).
Abbate et al., "Recurrent angina after coronary revascularization: a clinical challenge." Eur Heart J., 28:1057-65 (2007).
Abozguia et al. "Modification of myocardial substrate use as a therapy for heart failure." Nat Clin Pract Cardiovasc Med., 3:490-498 (2006).
Abozguia et al., "The heart metabolism: Pathophysiological aspects in ischaemia and heart failiure.", Curr Pharm Design, 15:827-835 (2009).
Arany et al, "Transcriptional coactivator PGC-1α controls energy state and contractile function of cardiac muscle", Cell Metabolism, 1: 259-271 (2005).
Arany et al., "Transverse aortic constriction leads to accelerated heart failure in mice lacking PPAR-γ coactivator 1α", PNAS, 103(26):10086-10091 (2006).
Ashrafian H. et al., "Metabolic mechanisms in heart failure", Circulation, 116:434-448 (2007).
Atherton JJ et al., "Diastolic ventricular interaction in chronic heart failure", Lancet, 349 (9067):1720-1724 (1997).
Auricchio et al., "Clinical efficacy of cardiac resynchronization therapy using left ventricular pacing in heart failure patients stratified by severity of ventricular conduction delay", J Am Coll Cardiol, 42(12):2109-2116 (2003).
Bacharach et al., "Left ventricular peak ejection rate, filling rate and ejection fraction-frame requirements at rest and exercise: concise communication", Journal of Nuclear Medicine, 20:189-193 (1979).
Baicu et al, "Left ventricular systolic performance, function, and contractility in patients with diastolic heart failure", Circulation; 111:2306-2312 (2005).
Bhatia et al., "Outcome of heart failure with preserved ejection fraction in a population-based study", N Engl J Med, 355:260-269 (2006).
Boden et al., "Optimal medical therapy with or without PCI for stable coronary disease" N Engl J Med, 356(15):1503-1516 (2007).
Bonnefont et al., "Carnitine palmitoyltransferases 1 and 2: biochemical, molecular and medicinal aspects". Mol Asp Med, 25:495-520 (2004).
Borlaug et al., "Impaired chronotropic and vasodilator reserves limit exercise capacity in patients with heart failure and a preserved ejection fraction", Circulation, 114:2138-2147 (2006).
Brubaker et al., "Chronotropic incompetence and its contribution to exercise intolerance in older heart failure patients", J Cardiopulm Rehabil, 26:86-89 (2006).
Bruce RA, McDonough JR, "Stress testing in screening for cardiovascular disease", Bull N Y Acad Med, 5(12):1288-1305 (1969).
Buffon et al., "Widespread coronary inflammation in unstable angina" N Engl J Med, 347(1):5-12 (2002).
Burkhoff et al., "Heart failure with a normal ejection fraction: is it really a disorder of diastolic function?", Circulation, 107:656-658 (2003).
Cavassila et al, "Cramer-Rao bounds: an evaluation tool for quantitation", NMR Biomed, 14:278-283 (2001).

(56) References Cited

OTHER PUBLICATIONS

Chatterjee et al., "Systolic and Diastolic Heart Failure: Differences and Similarities", *Journal of Cardiac Failure*, 13(7):569-576 (2007).
Chen et al., "Noninvasive single-beat determination of left ventricular end-systolic elastance in humans", *J Am Coll Cardiol*, 38:2028-2034 (2001).
Chirkov, YY, Horowitz JD, "Impaired tissue responsiveness to organic nitrates and nitric oxide: a new therapeutic frontier?", *Pharmacology & Therapeutics*, 116:287-305 (2007).
Cicoira et al., "Long-term, dose-dependent effects of spironolactone on left ventricular function and exercise tolerance in patients with chronic heart failure", *J Am Coll Cardiol*, 40(2):304-310 (2002).
Coats et al., "Current management of 1-8 hypertrophic cardiomyopathy", *Current Treatment Options in Cardiovascular Medicine*, 10:496-504 (2008).
Cohn, J., "The Management of Chronic Heart Failure", *New England Journal of Medicine*, 335(7):490-498(1996).
Cole et al., "Efficacy and safety of perhexiline maleate in refractory angina. A double-blind placebo-controlled clinical trial of a novel antianginal agent", *Circulation*, 81:1260-1270 (1990).
Cooper et al., "Studies on the metabolism of perhexiline in man", *Eur J Clin Pharmacol*, 32:569-576 (1987).
Cooper et al., "Polymorphic hydroxylation of perhexiline maleate in man", *J Med Genetics*, 21:27-33 (1984).
Czerwinski et al. "A controlled study of the diuretic and natriuretic of perhexiline maleate in normal human volunteers", *Postgraduate Medical Journal*, (Apr. Suppl.): 26-31 (1973).
Davies et al., "CYP2B6, CYP2D6, and CYP3A4 catalyze the primary oxidative metabolism of perhexiline enantiomers by human liver microsomes", *Drug Metab Dispos*, 35(1):128-138 (2007).
Davies et al, "Determination of the 4-monohydroxy metabolites of perhexiline in human plasma, urine and liver microsomes by liquid chromatography," *Journal of Chromatography B*, 843:302-309 (2006).
Davies et al., "Enantioselective assay for the determination of perhexiline enantiomers in human plasma by liquid chromatography", *Journal of Chromatography B*, 832: 114-120 (2006).
Davies et al., "Steady-state pharmacokinetics of the enantiomers of perhexiline in CYP2D6 poor and extensive metabolizers administered rac-perhexiline," *Br J Clin Pharmacol*, 65(3):347-354 (2008).
Davies NJ and Denison DM, "The measurement of metabolic gas exchange and minute volume by mass spectrometry alone", *Respiration Physiology*, 36(2):261-267 (1979).
Depre et al., "Glucose for the Heart", *Circulation*, 99:578-588 (1999).
Deschamps et al., "Inhibition by perhexiline of oxidative phosphorylation and the β-oxidation of fatty acids: possible role in pseudoalcoholic liver lesions", *Hepatology*, 19: 948-61 (1994).
Eckberg et al., "Defective cardiac parasympathetic control in patients with heart disease", *N Engl J Med*, 285(16):877-883 (1971).
Fardeau et al., "Muscle and nerve changes induced by perhexiline maleate in man and mice", *Muscle & Nerve*, 2:24-36 (1979).
Folmes et al., "High rates of residual fatty acid oxidation during mild ischaemia decrease cardiac work and efficiency", *J Mol Cell Cardiol*, 47:142-148 (2009).
Fragasso et al., "Effects of metabolic modulation by trimetazidine on left ventricular function and phosphocreatine/adenosine triphosphate ratio in patients with heart failure", *Eur Heart J*, 27:942-948 (2006).
Frenneaux, M, "New tricks for an old drug", *European Heart Journal*, 23:1898-1899 (2002).
Fromenty B, Pessayere D, "Inhibition of mitochondrial beta-oxidation as a mechanism of hepatotoxicity", *Pharmac Ther*; 67(1):101-154 (1995).
Fukuda et al., "Phosphorylation of Titin Modulates Passive Stiffness of Cardiac Muscle in a Titin Isoform-dependent manner", *J Gen Physiol*, 125:257-271 (2005).
Furst W and Hallstrom S, "Simultaneous determination of myocardial nucleotides, nucleosides, purine bases and creatine phosphate by ion-pair high-performance liquid chromatography", *J Chromatogr B*, 578: 39-44 (1992).
Gillebert et al., "Relaxation-systolic pressure relation: A load-independent assessment of left ventricular contractility", *Circulation*, 95:745-752 (1997).
Grossman et al., "Contractile state of the left ventricle in man as evaluated from end-systolic pressure-volume elations", *Circulation*, 56:845-852 (1977).
Heusch G., "Hibernating myocardium", *Physiol Rev*, 78(4):1055-1085 (1998).
Higginbotham et al., "Regulation of stroke volume during submaximal and maximal upright exercise in normal man", *Circ Res*, 58:281-291 (1986).
Holden K R, "Chronic Heart Failure and Disability" [Online] Aug. 7, 2007, *Disability Doc-Examining Social Security Disability*, Retrieved from the Internet: URL:http://www.disabilitydoc.com/chronic-heart~failure-and-disa/> (2007).
Horowitz et al., "Perhexiline maleate treatment for severe angina pectoris—correlations with pharmacokinetics", *Int J Cardiol*, 13:219-229 (1986).
Hulsmann et al., "Long-term effect of atenolol on ejection fraction, symptoms, and exercise variables in patients with advanced left ventricular dysfunction", *J Heart Lung Transplant*, 20:1174-1180 (2001).
Hunt et al., "ACC/AHA 2005 Guideline Update for the Diagnosis and Management of Chronic Heart Failure in the Adult: a report of the American College of Cardiology/American Heart Association Task Force on Practice Guidelines (Writing Committee to Update the 2001 Guidelines for the Evaluation and Management of Heart Failure): developed in collaboration with the American College of Chest Physicians and the International Society for Heart and Lung Transplantation: endorsed by the Heart Rhythm Society", *Circulation*, 112:e154-e235 available at www.acc.org (2005).
Inglis et al., "Effect of CYP2D6 metabolizer status on the disposition of the (+) and (−) enantiomers of perhexiline in patients with myocardial ischaemia", *Pharmacogenetics Genomics*, 17:305-312 (2007).
Ingwall JS and Weiss RG, "Is the failing heart energy starved?: On using chemical energy to support cardiac function", *Circulation Research*, 95:135-145 (2004).
Irvine et al., "Nitroxyl (HNO): the Cinderella of the nitric oxide story", *Trends in Pharmacol Sci*, 29(12):601-608 (2008).
Jeffrey et al, "Direct evidence that perhexiline modifies myocardial substrate utilization from fatty acids to lactate", *J Cardiovasc Pharmacol*, 25:469-472 (1995).
Kannel WB, "Incidence and epidemiology of heart failure", *Heart Failure Rev*, 5:167-173 (2000).
Kawaguchi et al., "Combined ventricular systolic and arterial stiffening in patients with heart failure and preserved ejection fraction: implications for systolic and diastolic reserve limitations", *Circulation*, 107:714-720 (2003).
Kennedy et al., "Effect of the anti-anginal agent, perhexiline, on neutrophil, valvular and vascular superoxide formation", *Eur J Pharmacol*, 531:13-19 (2006).
Kennedy et al., "Effect of perhexiline and oxfenicine on myocardial function and metabolism during low-flow ischemia/reperfusion in the isolated rat heart", *J Cardiovasc Pharmacol*, 36(6):794-801 (2000).
Kennedy et al., "Inhibition of carnitine palmitoyltransferase-1 in rat heart and liver by perhexiline and amiodarone", *Biochem Pharmacol*, 52:273-280 (1996).
Killalea SM and Krum H, "Systematic review of the efficacy and safety of perhexiline in the treatment of ischemic heart disease", *Am J Cardiovasc Drugs*, 1(3):193-204 (2001).
Kiriazis H and Kranias EG, "Genetically engineered models with alterations in cardiac membrane calcium-handling proteins", *Annu Rev Physiol*, 62:321-351 (2000).
Kitakaze, Masashi et al., "New role of adenosine for the treatment of ischemic heart disease", *Journal of Clinical and Experimental Medicine* (Igaku No Ayumi), 192(1):35-39 (2000).
Lamb et al., "Diastolic dysfunction in hypertensive heart disease is associated with altered myocardial metabolism", *Circulation*, 99:2261-2267. (1999).

(56) References Cited

OTHER PUBLICATIONS

Lang et al., "Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology", J Am Soc Echocardiogr, 18:1440-1463 (2005).

Lee et al., "Metabolic manipulation of ischaemic heart disease, a novel approach to treatment", Eur Heart J, 25:634-641 (2004).

Lee et al., "Metabolic modulation with perhexiline in chronic heart failure: a randomized, controlled trial of short-term use of a novel treatment", Circulation, 112:3280-3288 (2005).

Lee et al., "Augmentation of Glucose Metabolism With Perhexiline Improves Maximal Oxygen Consumption and Quality of Life in Patients With Nonischaemic Dilated Cardiomyopathy", Journal of the American College of Cardiology, 43(5): 190-A-1088-122(2004).

Leite-Moreira et al., "Afterload induced changes in myocardial relaxation: a mechanism for diastolic dysfunction", Cardiovasc Res, 43:344-353 (1999).

Lele et al., "Determinants of exercise capacity in patients with coronary artery disease and mild to moderate systolic dysfunction. Role of heart rate and diastolic filling abnormalities", Eur Heart J, 17(2):204-212 (1996).

Lele et al., "Exercise capacity in hypertrophic cardiomyopathy. Role of stroke volume limitation, heart rate, and diastolic filling characteristics", Circulation, 92:2886-2894 (1995).

Liberts et al., "Effects of perhexiline and nitroglycerin on vascular, neutrophil and platelet function in patients with stable angina pectoris", Eur J Pharmacol, 560: 49-55 (2007).

Lindahl et al., "Markers of myocardial damage and inflammation in relation to long-term mortality in unstable coronary artery disease", N Engl J Med, 343: 1139-1147 (2000).

Lopaschuk et al., "An imbalance between glycolysis and glucose oxidation is a possible explanation for the detrimental effects of high levels of fatty acids during aerobic reperfusion of ischemic hearts", J Pharmacol Exp Ther, 264(1):135-144 (1993).

Magorien et al., "Hemodynamic correlates for timing intervals, ejection rate and filling rate derived from the radionuclide angiographic volume curve", Am J Cardiol, 53:567-571 (1984).

Mann, DL, "Mechanisms and Models in Heart Failure: A Combinatorial Approach", Circulation, 100:999-1008 (1999).

Mannheimer et al., "The problem of chronicrefractory angina", Eur Heart J, 23: 355-370 (2002).

Mantero et al., "Left ventricular diastolic parameters in 288 normal subjects from 20 to 80 years old", Eur Heart J, 16:94-105 (1995).

Metra et al., "Treatment of advanced chronic heart failure with normal left ventricular ejection fraction. Response to the letter by Dr. Martinez-Selles", European Journal of Heart Failure, 9(12)1224-1225 (2007).

Metra et al., "Advanced chronic heart failure: A position statement from the Study Group on Advanced Heart Failure of the Heart Failure Association of the European Society of Cardiology", European Journal of Heart Failure, 9:684-694 (2007).

Morgan et al., "Impaired oxidation of debrisoquine in patients with perhexiline liver injury", Gut, 25: 1057-1064 (1984).

Murnaghan MF, "Effect of fatty acids on the ventricular arrhythmia threshold in the isolated heart of the rabbit", Br J Pharmacol, 73(4):909-915 (1981).

Najjar et al., "Age and gender affect ventricular-vascular coupling during aerobic exercise", J Am Coll Cardiol, 44:611-617 (2004).

Naressi et al., "Java-based graphical user interface for MRUI, a software package for quantitation of in vivo/medical magnetic resonance spectroscopy signals", Comput Biol Med, 31(4):269-286 (2001).

Neubauer et al., "31P magnetic resonance spectroscopy in dilated cardiomyopathy and coronary artery disease. Altered cardiac high-energy phosphate metabolism in heart failure", Circulation, 86(6):1810-1818 (1992).

Neubauer et al., "Myocardial phosphocreatine-to-ATP ratio is a predictor of mortality in patients with dilated cardiomyopathy", Circulation, 96:2190-2196 (1997).

Neubauer et al., "Contributions of 31P-magnetic resonance spectroscopy to the understanding of dilated heart muscle disease", Eur Heart J, 16(Suppl O):115-118 (1995).

Neubauer S, "The failing heart—an engine out of fuel", N Engl J Med, 356: 1140-1151 (2007).

Nihoyannopoulos et al., "Diastolic function in hypertrophic cardiomyopathy: relation to exercise capacity", J Am Coll Cardiol, 19:536-540 (1992).

O'Brien et al., "Cardiac troponin I is a sensitive, specific biomarker of cardiac injury in laboratory animals", Laboratory Animals; 40:153-171 (2006).

Ommen et al., "Clinical utility of Doppler echocardiography and tissue Doppler imaging in the estimation of left ventricular filling pressures: A comparative simultaneous Dopplercatheterization study", Circulation, 102:1788-1794 (2000).

Ordidge et al, "Separate water and fat MR images", Letters to the Editor, Radiology, 157(2):551-553 (1985).

Peltier et al., "Treatment practices in heart failure with preserved left ventricular ejection fraction: A prospective observational study", International Journal of Cardiology, 118(3):363-369 (2007).

Pena JR and Wolska BM, "Troponin I phosphorylation plays an important role in the relaxant effect of β-adrengergic stimulation in mouse hearts", Cardiovasc Res, 61:756-763 (2004).

Pepine et al., "Alteration of left ventricular responses to ischemia with oral perhexiline", Postgraduate Medical Journal, April Suppl:43-46 (1973).

Pepine et al., "Effects of perhexiline on coronary hemodynamic and myocardial metabolic responses to tachycardia", Circulation, 49:887-893 (1974).

Perseghin et al., "Left ventricular function and energy metabolism in middle-aged men undergoing long lasting sustained aerobic oxidative training", Heart Online (downloaded from heart.bmj.com—Nov. 21, 2008) doi:10.1136/hrt.2008.154716 (published online Nov. 13, 2008).

Phan et al., "Dynamic changes in left ventricular function on exercise in heart failure with preserved ejection fraction: the role of myocardial energy deficiency", Heart, 95:114 (2009).

Phan et al., "Heart Failure With Preserved Ejection Fraction is Characterized by Dynamic Impairment of Active Relaxation and Contraction of the Left Ventricle on Exercise and Associated With Myocardial Energy Deficiency", J. Am. Coll. Cardiol., 54:402-409 (2009).

Porrello et al, "Heritable pathologic cardiac hypertrophy in adulthood is preceded by neonatal cardiac growth restriction", Am J Physiol Regul Integr Comp Physiol, 296:R672-R680 (2009).

Poupon et al., "Perhexiline maleate-associated hepatic injury prevalence and characteristics", Digestion, 20: 145-150 (1980).

Ritchie et al., "Exploiting cGMP-based therapies for the prevention of left ventricular hypertrophy: NO & beyond", Pharmacol Ther, 124:279-300 (2009).

Ritchie et al., "B-type Natriuretic Peptide: Endogenous regulator of myocardial structure, biomarker and therapeutic target", Curr Mol Med, 9:814-25 (2009).

Robertson et al., "The effect of troponin I phosphorylation on the $Ca^{2+}$-binding properties of the $Ca^{2+}$-regulatory site of bovine cardiac troponin", J Biol Chem, 257(1):260-263 (1982).

Rossi et al., "Chronic heart failure with preserved left ventricular ejection fraction: Diagnostic and prognostic value of left atrial size", International Journal of Cardiology, 110(3):386-392 (2006).

Rupp et al, "The use of partial fatty acid oxidation inhibitors for metabolic therapy of angina pectoris and heart failure", Herz, 27:621-636 (2002).

Sallustio et al., "Pharmacokinetics of the antianginal agent perhexiline: relationship between metabolic ratio and steady-state dose", Br J Clin Pharmacol, 54:107-14 (2002).

Scheuermann-Freestone et al., "Abnormal cardiac muscle function in heart failure is related to insulin resistance", Cardiovasc J S Afr, 15(4 Suppl 1):12, #52 (2004).

(56) References Cited

OTHER PUBLICATIONS

Scheuermann-Freestone et al., "Abnormal cardiac and skeletal muscle energy metabolism in patients with type 2 diabetes", *Circulation*, 107:3040-3046 (2003).
Seth et al., "Alterations in isoproterenol-induced cardiac metabolic changes by perhexiline", *Indian J Med Res*, 81:224-229 (1985).
Shinke, Toshirou, "Treatment of Heart Failure Associated With Ischemic Heart Disease", *Clinical Practice and Study*, 78(9):73-79 (2001).
Shivu et al., "31P magnetic resonance spectroscopy to measure in vivo cardiac energetics in normal myocardium and hypertrophic cardiomyopathy: Experiences at 3T", *Eur J Radiol*, 73:255-259 (2010).
Singlas et al., "Pharmacokinetics of perhexiline maleate in anginal patients with and without peripheral neuropathy", *Eur J Clin Pharmacol*, 14:195-201 (1978).
Smith et al., "Altered creatine kinase adenosine triphosphate kinetics in failing hypertrophied human myocardium", *Circulation*, 114:1151-1158 (2006).
Stanley et al., "Myocardial substrate metabolism in the normal and failing heart", *Physiol Rev*, 85:1093-129 (2005).
Stewart et al., "More 'malignant' than cancer? Five-year survival following a first admission for heart failure", *Eur J Heart Fail*, 3:315-322 (2001).
Stewart et al., "Relationship between plasma perhexiline concentration and symptomatic status during short-term perhexiline therapy", *Ther Drug Monit*, 18:635-639 (1996).
Szibor M and Holtz J, "Mitochondrial ageing", *Basic Res Cardiol*, 98:210-218 (2003).
Takei, Kumiko et al., "Three Cases of Acute Exacerbation of Chronic Heart Failure Treated With Milrinone", *Therapeutic Research*, 20(8):245-251 (1999).
Takimoto et al., "Frequency-and afterload-dependent cardiac modulation in vivo by troponin I with constitutively active protein kinase A phosphorylation sites", *Circ Res*, 94:496-504 (2004).
Teerlink et al., "Progressive ventricular remodeling in response to diffuse isoproterenol-induced myocardial necrosis in rats", *Circ Res*, 75:105-113 (1994).
Teo et al., "Perhexiline during exercise training in coronary heart disease", *Clinical Pharmacology and Therapeutics*, 34(6):744-748 (1983).
Unger et al., "Dissociation between metabolic and efficiency effects of perhexiline in normoxic rat myocardium", *J Cardiovasc Pharmacol*, 46:849-855 (2005).
Unger et al., "Perhexiline improves symptomatic status in elderly patients with severe aortic stenosis", *Aust NZ J Med*, 27:24-28 (1997).
Vasan et al., "Prevalence, clinical features and prognosis of diastolic heart failure: an epidemiologic perspective", *JACC*, 26(7):1565-1574 (1995).
Vescovo et al., "Improved exercise tolerance after losartan and enalapril in heart failure: correlation with changes in skeletal muscle myosin heavy chain composition", *Circulation*, 98(17):1742-1749 (1998).
Westermann et al., "Role of left ventricular stiffness in heart failure with normal ejection fraction", *Circulation*, 117:2051-2060 (2008).
Willoughby et al., "Beneficial clinical effects of perhexiline in patients with stable angina pectoris and acute coronary syndromes are associated with potentiation of platelet responsiveness to nitric oxide", *Eur Heart J*, 23:1946-1954 (2002).
Willoughby et al., "Platelet nitric oxide responsiveness: a novel prognostic marker in acute coronary syndromes", *Arterioscler Thromb Vasc Biol*, 25: 2661-2666 (2005).
Wright et al., "The absorption, excretion and metabolism of perhexiline maleate by the human", *Postgrad Med J*, 49 (April Suppl 3):8-15 (1973).
Yagi et al., "Sustained currents through ASIC3 ion channels at the modest pH changes that occur during myocardial ischemia", *Circ Res*, 99:501-509 (2006).
Yang et al., "Current and future treatment strategies for refractory angina", *Mayo Clin Proc*, 79(10):1284-1292 (2004).
Yu et al., "Progression of systolic abnormalities in patients with "isolated" diastolic heart failure and diastolic dysfunction", *Circulation*, 105:1195-1201 (2002).
Zanger et al., "Cytochrome P450 2D6: overview and update on pharmacology, genetics and biochemistry", *Naunyn-Schmiedeberg's Arch Pharmacol*, 369:23-37 (2004).
Zhang et al, "Cardiac troponin I phosphorylation increases the rate of cardiac muscle relaxation", *Circ Res*, 76:1028-1035 (1995).
Zile et al., "Diastolic heart failure—abnormalities in active relaxation and passive stiffness of the left ventricle", *N Engl J Med*, 350:1953-1959 (2004).
Zile MR and Brutsaert DL, "New concepts in diastolic dysfunction and diastolic heart failure: Part I: diagnosis, prognosis, and measurements of diastolic function", *Circulation*, 105:1387-1393 (2002).
Notification of Reasons for Refusal issued in JP 2007-502376, (with English translation) Jan. 12, 2011.
"View of NCT00500552 on Jul. 11, 2007," <https://clinicaltrials.gov/archive/NCT00500552/2007_07_11>, retrieved on Mar. 9, 2015 (3 pages).
"View of NCT00839228 on Feb. 8, 2009," <https://clinicaltrials.gov/archive/NCT00839228/2009_02_08>, retrieved on Mar. 18, 2015 (3 pages).
Ashrafian et al., "Perhexiline," Cardiovasc Drug Rev. 25(1):76-97 (2007).
Butera et al., "Heart rate variability in children with hypertrophic cardiomyopathy," Heart. 89(2):205-6 (2003).
De Keulenaer et al., "Systolic and diastolic heart failure: different phenotypes of the same disease?" Eur J Heart Fail. 9(2):136-43 (2007).
Dostal et al., "Understanding diastolic heart failure with preserved ejection fraction: choosing the right model," Hypertension. 47(5):830-2 (2006).
Drexler et al., "Explaining fatigue in congestive heart failure," Annu Rev Med. 47:241-56 (1996).
Gersh et al., "2011 ACCF/AHA guideline for the diagnosis and treatment of hypertrophic cardiomyopathy: executive summary: a report of the American College of Cardiology Foundation/American Heart Association Task Force on Practice Guidelines," J Am Coll Cardiol. 58(25): 2703-38 (2011).
Gould et al., "Stereoselective pharmacokinetics of perhexiline," Xenobiotica. 16(5):491-502 (1986).
Hunt et al., "ACC/AHA Guidelines for the Evaluation and Management of Chronic Heart Failure in the Adult: Executive Summary a Report of the American College of Cardiology/American Heart Association Task Force on Practice Guidelines (Committee to Revise the 1995 Guidelines for the Evaluation and Management of Heart Failure)," Circulation. 104(24):2996-3007 (2001).
Jerant et al., "Reducing the cost of frequent hospital admissions for congestive heart failure: a randomized trial of a home telecare intervention," Med Care. 39(11):1234-45 (2001).
Krum et al., "Guidelines for management of patients with chronic heart failure in Australia," Med J Aust. 174(9):459-466 (2001).
Krum et al., "Guidelines for the prevention, detection and management of people with chronic heart failure in Australia 2006," Med J Aust. 185(10):549-56 (2006).
Maron et al., "Usefulness of B-Type natriuretic peptide assay in the assessment of symptomatic state in hypertropic cardiomyopathy," Circulation. 109(8):984-989 (2004).
Mayo Clinic Staff, "Heart Failure: Causes," <www.mayoclinic.org/diseases-conditions/heart-failure/basics/causes/con-20029801>, retrieved Nov. 11, 2015 (4 pages).
Sasson et al., "Causal relation between the pressure gradient and left ventricular ejection time in hypertrophic cardiomyopathy," J Am Coll Cardiol. 13(6):1275-9 (1989).
Shah, "Hypertrophic cardiomyopathy and diastolic dysfunction," J Am Coll Cardiol. 42(2):286-7 (2003).
Williams et al., "Syncope in hypertrophic cardiomyopathy: mechanisms and consequences for treatment," Europace. 9(9):817-22 (2007).

(56) References Cited

OTHER PUBLICATIONS

Decision of Refusal for Japanese Application No. 2012-510371, dated Apr. 14, 2015 (8 pages).
Decision on Rejection for Chinese Application No. 201080032444.3, dated on Apr. 27, 2015 (10 pages).
Demand for a Trial for Japanese Patent Application No. 2012-511329, filed on Apr. 1, 2015 (2 pages).
EPO Communication for European Patent Application No. 10720191.5, dated Jan. 23, 2015 (4 pages).
Examination Report for Australian Patent Application No. 2010247120, issued Aug. 19, 2014 (3 pages).
Examination Report for Canadian Patent Application No. 2,799,087, mailed Jul. 10, 2015 (4 pages).
Examiner's Report for New Zealand Patent Application No. 597031, dated Sep. 17, 2012 (2 pages).
Final Rejection for U.S. Appl. No. 14/186,554, dated Apr. 16, 2015 (15 pages).
First Examination Report for Australian Patent Application No. 2009346606, dated Aug. 18, 2014 (3 pages).
First Examination Report for New Zealand Patent Application No. 625344, dated May 22, 2014 (2 pages).
Fourth Office Action for Chinese Patent Application No. 200980160678.3, mailed Mar. 3, 2016 (11 pages).
Further Examination Report for New Zealand Patent Application No. 597031, dated Mar. 5, 2014 (2 pages).
International Preliminary Report on Patentability and Written Opinion for PCT/GB2008/003919, dated Jun. 1, 2010 (11 pages).
International Preliminary Report on Patentability for International Patent Application No. PCT/GB2010/050770, issued Nov. 15, 2011 (4 pages).
International Search Report and Written Opinion for International Patent Application No. PCT/AU2013/001008, mailed on Nov. 6, 2013 (10 pages).
International Search Report for International Patent Application No. PCT/GB2010/050770, mailed Jul. 22, 2010 (2 pages).
International Search Report for PCT/GB2008/003913, mailed Apr. 1, 2009 (4 pages).
International Search Report for PCT/GB2009/050539, mailed Nov. 9, 2009 (5 pages).
Non-Final Rejection for U.S. Appl. No. 13/838,458, dated Nov. 16, 2015 (9 pages).
Notice of Reasons for Refusal for Japanese Patent Application No. 2012-511329, dated Dec. 3, 2013 (6 pages).
Notification of Reasons for Refusal for Japanese Patent Application No. 2015-075231, mailed Mar. 1, 2016 (4 pages).
Office Action for Chinese Patent Application No. 200980160678.3, dated Jan. 30, 2013 (4 pages).
Office Action for Chinese Patent Application No. 201080032444.3, dated Nov. 21, 2012 (5 pages).
Office Action for European Application No. 10720191.5, dated Jul. 28, 2015 (4 pages).
Office Action for European Patent Application No. 10720191.5, dated Aug. 27, 2013 (3 pages).
Office Action for European Patent Application No. 10720191.5, dated Jan. 23, 2015 (4 pages).
Office Action for Israeli Patent Application No. 216288, dated Sep. 15, 2014 (7 pages) (English Translation).
Office Action for Israeli Patent Application No. 216362, dated Sep. 9, 2014 (8 pages).
Office Action for Japanese Patent Application No. 2012-510371, dated Jun. 17, 2014 (6 pages).
Office Action for Mexican Application No. MX/a/2011/012131, dated Jun. 1, 2015 (5 pages).
Office Action for Mexican Patent Application No. MX/a/2011/012131, dated Mar. 27, 2014 (7 pages).
Second Office Action for Chinese Patent Application No. 200980160678.3, dated Dec. 2, 2013 (6 pages).
Second Office Action for Chinese Patent Application No. 2010800324443, dated Sep. 29, 2013 (13 pages) (English translation Included).
Third Office Action for Chinese Patent Application No. 201080032444.3, dated Jun. 10, 2014 (8 pages) (English translation Included).
Third Office Action for Chinese Patent Application No. 200980160678.3, dated Oct. 31, 2014 (8 pages).

\* cited by examiner

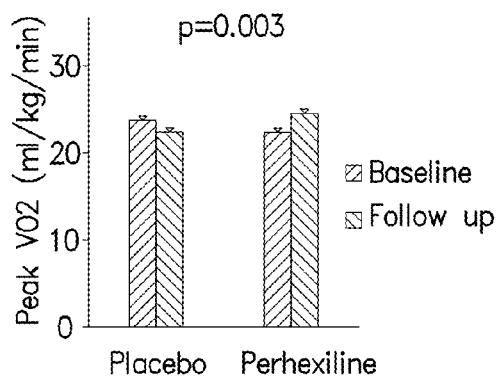 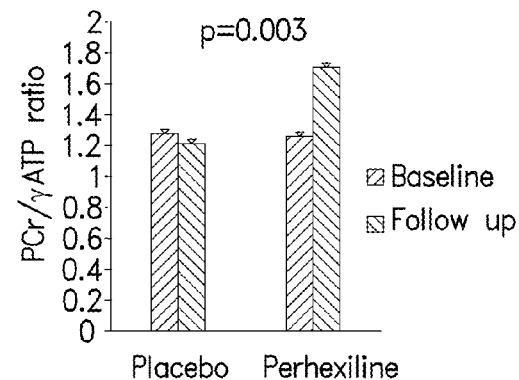
FIG. 5A  FIG. 5B
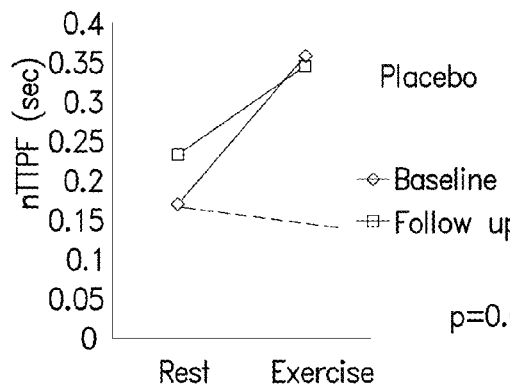 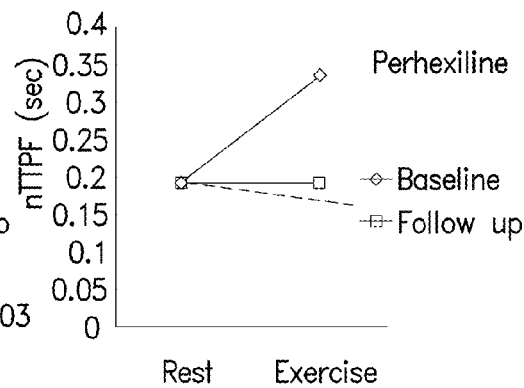
FIG. 5C  FIG. 5D
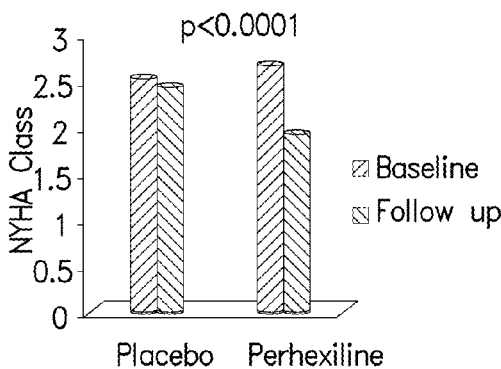 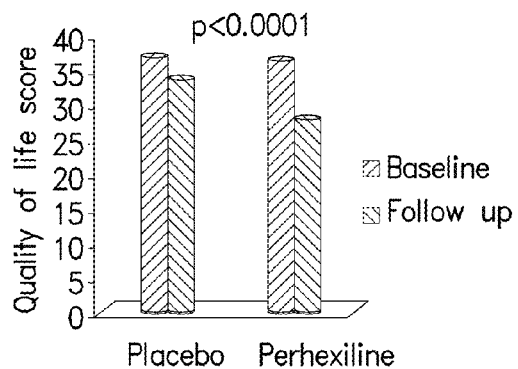
FIG. 5E  FIG. 5F

TREATMENT OF HEART FAILURE

CROSS-REFERENCE TO RELATED APPLICATIONS

This application is a continuation of U.S. application Ser. No. 12/785,077, filed May 21, 2010, which is (1) a continuation-in-part of International Application No. PCT/GB2008/003913, filed Nov. 24, 2008, which claims the benefit of GB Application No. 0723100.4, filed Nov. 23, 2007, and the benefit of U.S. Application No. 60/990,933, filed Nov. 29, 2007, and (2) a continuation of International Application No. PCT/GB2009/050539, filed May 20, 2009. The entire contents of each of the above-identified applications are incorporated herein by reference.

BACKGROUND OF THE INVENTION

Significant advances in therapy for heart failure (HF) with impaired systolic function have improved quality of life, and increased survival. However up to 50% of patients who have clinical evidence of HF are found to have a relatively (or near) normal left ventricular ejection fraction (HF with normal left ventricular (LV) ejection fraction syndrome (HFnEF), also referred to as HF with preserved left ventricular ejection fraction syndrome (HFpEF). Patients with HFnEF represent a rapidly increasing proportion of patients hospitalised and suffering mortality from heart failure.

Despite a normal EF, HFnEF patients manifest subtle systolic dysfunction but the principal abnormality in most is a disorder of active relaxation and/or passive filling of the LV. However resting measures of active relaxation and filling relate poorly to symptoms and exercise capacity therefore no 'gold standard' diagnostic echocardiographic test exists for HFnEF. Effective ventricular filling results from a highly energy dependent active relaxation process and from passive filling which is dependent on loading conditions as well as the intrinsic (passive) properties of the LV. Since both these parameters change markedly during exercise due to sympathetic activation, it is not surprising that these resting parameters are so poorly predictive of exercise capacity and symptoms.

The treatment of patients with HFnEF is discussed in Hunt et al., "ACC/AHA 2005 Guideline Update for the Diagnosis and Management of Chronic Heart Failure in the Adult", 2005, Section 4.3.2, available at www.acc.org.

Perhexiline (2-(2,2-dicyclohexylethyl)piperidine) is a known anti-anginal agent that operates principally by virtue of its ability to shift metabolism in the heart from free fatty acid metabolism to glucose, which is more energy efficient.

WO-A-2005/087233 discloses the use of perhexiline for the treatment of chronic heart failure (CHF) where the CHF is a result of an initial inciting influence of ischaemia or where the CHF is a result of an initial non-ischaemic inciting influence.

SUMMARY OF THE INVENTION

According to a first aspect of the present invention, there is provided a method of treating HFnEF, which comprises administering to an animal in need thereof an effective amount of perhexiline, or a pharmaceutically acceptable salt thereof, to treat said HFnEF. The animal is preferably a mammal and most preferably a human.

According to another aspect of the present invention, perhexiline, or a pharmaceutically acceptable salt thereof, is provided for use in the treatment of HFnEF.

According to a further aspect of the invention there is provided a treatment programme for treating HFnEF, which involves the co-use or co-administration of perhexiline or pharmaceutically acceptable salt thereof with one or more other compounds that are advantageous in treating HFnEF or the symptoms thereof, for example a diuretic, an angiotensin receptor blocker or a calcium channel blocker.

BRIEF DESCRIPTION OF THE DRAWINGS

FIG. 4A represents the peak oxygen consumption (peak $VO_2$max) results;

FIG. 4B represents the diastolic ventricular filling results (nTTPF, normalized for heart rate Time To Peak Filling) and shows that PCr/γATP ratio (a measure of cardiac energetic state) is lower in HCM patients versus controls;

FIG. 4C is an example of $^{31}P$ cardiac spectra of a HCM patient in which Point C indicates centre of phosphorus coil, VOI; voxel of interest, 2,3-DPG indicates 2,3-diphosphoglycerate; PDE, phosphodiesters; PCr, phosphocreatine; α, β, γ indicate the three phosphorus nuclei of ATP, and shows that nTTPF (a measure of the rate of active relaxation of the LV) is essentially unchanged on exercise in the controls bu abnormally slows in the HCM patients; and FIG. 4D represent the myocardial energetic results (PCr/γATP ratio) and shows that exercise capacity (peak $VO_2$) is lower in HCM patients versus controls.

FIGS. 5A and 5B respectively represent the effect of Placebo and Perhexiline on peak oxygen consumption (peak $VO_2$), p=0.003 and myocardial energetic (PCr/γATP ratio), p=0.003, where the p value represents the significant difference between perhexiline and placebo response. Peak $VO_2$ (exercise capacity) increases with Perhexiline (FIG. 5A). Perhexiline improves PCr/γATP ratio (energetic status of heart), but this was unchanged in the placebo group (FIG. 5B).

FIGS. 5C and 5D respectively represent nTTPF changes in the placebo group (3C) and the perhexiline group (3D), p=0.03, where the p value represents the significant difference between perhexiline and placebo response. In the placebo group nTTPF (a measure of the rate of LV active relaxation) abnormally lengthened at baseline and on treatment. The response in healthy controls is shown in dotted lines. Perhexiline (FIG. 5D) normalises the response to similar to that seen in healthy controls (also shown in dotted lines).

FIGS. 5E and 5F illustrate that NYHA score (of breathlessness) falls (improves) with perhexiline (5E) and Minnesota living with heart failure questionnaire score falls (=improved quality of life) on perhexiline (5F).

DETAILED DESCRIPTION OF THE INVENTION

Figure 1A:
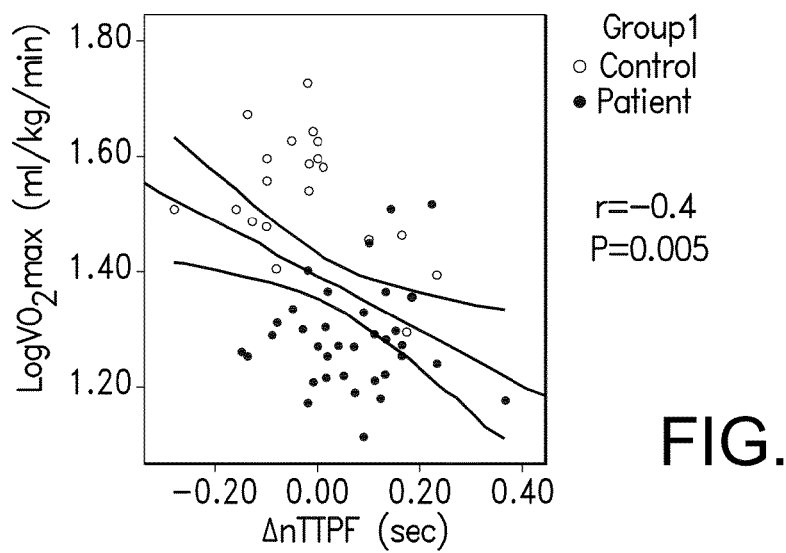
FIGS. 1A-1C displays variables correlating with Aerobic Exercise Capacity ($VO_2$max) in HFnEF patients and controls.

The findings of the study reported in Example 1 herein are that a) HFpEF patients manifest a significant reduction in PCr/γATP ratio at rest, indicating impairment of myocardial energy 'reserves' and b) during exercise, the energetically demanding active relaxation stage of diastole lengthened in patients (vs. a shortening in controls) and there was also a failure of contractile function to increase in patients. These abnormalities together resulted in a lower stroke volume on exercise. It was also found that HFpEF patients demonstrated chronotropic incompetence on exercise.

These findings correlate closely with findings in a study of patients with hypertrophic cardiomyopathy (HCM), which is reported in Example 2. The study of Example 2 also demonstrated the effectiveness of the agent perhexiline in the treatment of patients with HCM. Because of the related pathophysiology of HFnEF and HCM, the inventors are able to predict, based on the effectiveness of perhexiline in the treatment of HCM, that this same agent will be an effective therapeutic agent for treatment of HFnEF.

In aspects of the present invention, the perhexiline exists in the form of a salt of perhexiline, preferably the maleate salt. The perhexiline may be used at doses titrated to achieve therapeutic but non-toxic plasma perhexiline levels (Kennedy J A, Kiosoglous A J, Murphy G A, Pelle M A, Horowitz J D. "Effect of perhexiline and oxfenicine on myocardial function and metabolism during low-flow ischemia/reperfusion in the isolated rat heart", J Cardiovasc Pharmacol 2000; 36(6):794-801). Typical doses for a normal patient would be 100 mg to 300 mg daily, although smaller doses may be appropriate for patients who are slow metabolisers of perhexiline.

Physiologically acceptable formulations, such as salts, of the compound perhexiline, may be used in the invention. Additionally, a medicament may be formulated for administration in any convenient way and the invention therefore also includes within its scope use of the medicament in a conventional manner in a mixture with one or more physiologically acceptable carriers or excipients. Preferably, the carriers should be "acceptable" in the sense of being compatible with the other ingredients of the formulation and not deleterious to the recipient thereof. The medicament may be formulated for oral, buccal, parental, intravenous or rectal administration. Additionally, or alternatively, the medicament may be formulated in a more conventional form such as a tablet, capsule, syrup, elixir or any other known oral dosage form.

The invention is illustrated by the following non-limiting examples.

EXAMPLE 1

The role of exercise related changes was evaluated in left ventricular (LV) relaxation and of vasculo-ventricular coupling as the mechanism of exercise limitation in patients with heart failure with normal (or preserved) LV ejection fraction (HFnEF) and whether cardiac energetic impairment may underlie these abnormalities.

The study involved 37 patients with HFpEF and 20 matched controls. Vasculo-ventricular coupling (VVC) and Time to Peak LV Filling (a measure of LV active relaxation) (nTTPF) were assessed at rest and on exercise by Multiple Uptake Gated Acquisition scanning. Cardiac energetic status (PCr/γATP ratio) was assessed by $^{31}$P Magnetic Resonance Spectroscopy. At rest nTTPF and VVC were similar in patients and controls. Cardiac PCr/γATP ratio was reduced in patients vs. controls (1.57±0.52 vs. 2.14±0.62; P=0.003). VO$_2$max was lower in patients vs. controls (19±4 vs. 36±8 ml/kg/min; P<0.001). During maximal exercise the heart rate increased less in patients vs. controls (52±16 vs. 81±14 bpm; p<0.001) and the relative changes in stroke volume and cardiac output during submaximal exercise were lower in patients vs. controls (0.99±0.34 vs. 1.25±0.47, P=0.04; 1.36±0.45 vs. 2.13±0.72, P<0.001). nTTPF fell during exercise in controls, but increased in patients (−0.03±12 sec vs. +0.07±0.11; P=0.005). VVC decreased on exercise in controls but was unchanged in patients (−0.01±0.15 vs. −0.25±0.19; p<0.001). Heart rate, VVC and nTTPF were independent predictors of VO$_2$max.

Methods

Patients

The study involved 37 HFpEF patients prospectively recruited from heart failure clinics. Also studied were twenty age-gender-matched healthy controls with no cardiac history or diabetes mellitus. Study participants had clinical examination, 12-lead electrocardiogram, pulmonary function test, echocardiogram, metabolic exercise test, radionuclide ventriculography and a subgroup underwent cardiac $^{31}$P MRS studies to assess cardiac energetic status. All controls had a normal cardiovascular examination, 12-lead electrocardiogram and echocardiogram. HFpEF patients were defined in accordance with ACC/AHA recommendation (1): i) symptoms and signs of heart failure, ii) ejection fraction ≥50%, iii) no valvular abnormalities. In addition it was stipulated that patients should have iv) VO$_2$max <80% of age and gender predicted with a pattern of gas exchange on metabolic exercise testing indicating a cardiac cause for limitation, v) absence of objective evidence of lung disease on formal lung function testing and/or absence of arterial desaturation during exercise and with a ventilatory reserve at peak exercise ≥15 L. This definition was chosen in order to have robust evidence that patients had exercise limitation that was cardiac rather than non cardiac in origin and so as not to prejudge the underlying pathophysiology by stipulating the presence of resting diastolic abnormalities because mild diastolic abnormlities are frequently present also in healthy elderly subjects and moderate to severe resting diastolic abnormalities are frequently not present in patients with clear evidence of HFpEF. Patients with rhythm other than sinus were excluded.

Echocardiography

Echocardiography was performed with participants in the left lateral decubitus position with a Vivid 7 echocardiographic machine using a 2.5-MHz transducer. Cardiac quantifications were determined in accordance with European Association of Echocardiography. (2) LV end-systolic elastance (Ees), a measure of LV contractility, was determined using the non-invasive single-beat technique. (3) Arterial elastance (Ea), a measure of the stiffness of the entire arterial tree, was calculated as the ratio of LV end-systolic pressure/stroke volume. Studies were stored digitally and analyzed off-line.

$^{31}$P Cardiac Magnetic Resonance Spectroscopy (MRS)

In vivo myocardial energetics was measured by MRS at 3-Tesla (4). $^{31}$P cardiac magnetic resonance spectroscopy was performed using a Phillips Achieva 3T scanner and a linearly polarized transmitter and receiver $^{31}$P coil with a diameter of 14 cm. The repetition time was 10000 ms with 136 averages and 512 samples. Acquisition was ECG gated and the trigger delay was set to acquire in diastole. Total scan time was 23 minutes (5). Java magnetic resonance user interface v3.0 (jMRUI) was used for analysis. PCr and γ-ATP was used to determine the PCr/γATP ratio which is a measure of cardiac energetic state (6). Patients with ischemic heart disease and diabetes (N=7) were excluded from the MRS studies because these conditions are known to have impaired cardiac energetics (7,8). Patients with contraindications were also excluded from the MRS study (N=5). One patient's spectra was excluded from the analysis due to poor quality. Three controls had contraindication to MRS study. Data were analysed separately by an investigator unaware of participants' clinical status.

Radionuclide Ventriculography

LV ejection fraction and diastolic filling were assessed by radionuclide ventriculography at rest and during graded semi erect exercise on a cycle ergometer as previously described. (9,10) Three minutes of data were acquired at rest and during exercise after a 30-second period for stabilisation of heart rate at the commencement of each stage. Exercise was performed at 50% workloads of heart rate reserve. Data were analysed using LinkMedical MAPS software, Sun Microsystems (Hampshire, UK). Peak left ventricular filling rate in terms of end-diastolic count per second (EDC/s) and time to peak filling normalised for R-R interval (nTTPF) in milliseconds after end systole were calculated from the first derivative of the diastolic activity-time curve. Venous blood samples were obtained for weighing and for counting of blood gamma activity during each scan in order to correct for physical and physiological decay as well as for determination of relative volume changes. (11) The validity of these radionuclide measures of diastolic filling at high heart rates has been established previously. (12)

All gated blood pool scan-derived volumes were normalized to body surface area, yielding their respective indexes: end-diastolic volume index (EDVI), end-systolic volume index (ESVI), stroke volume index (SVI), and cardiac index. The following indexes were calculated: a) arterial elastance index (EaI)=ESP/SVI; b) LV end-systolic elastance index (ELVI)=ESP/ESVI and c) vasculo-ventricular coupling ratio (VVC)=EaI/ELVI=(1/EF)−1. (13)

Metabolic Exercise Test

All participants underwent a symptom-limited erect treadmill exercise using a standard ramp protocol with simultaneous respiratory gas analysis. (14)

Statistics

Continuous variables are expressed as means±SD. Unpaired Student's t-test (2-tail) was used to assess differences between mean values. Categorical variables were compared with Pearson Chi-Square test. All reported P values were calculated on the basis of two sided tests and a P value of <0.05 was considered to indicate statistical significance. Variances of data sets were determined using F-test. Pearson correlation coefficient (r) was used to describe the relationship between variables. All subjects were included into the model. Variables of interest that were found to correlate with the dependent variable on univariate analysis were included in a stepwise linear regression analysis to identify independent variables. SPSS (v15.0) was used to perform the statistical operations.

Results

The results obtained are set forth in Tables 1-3 below and in FIGS. 1A-1C and 2A-2D.

Figure 1B:
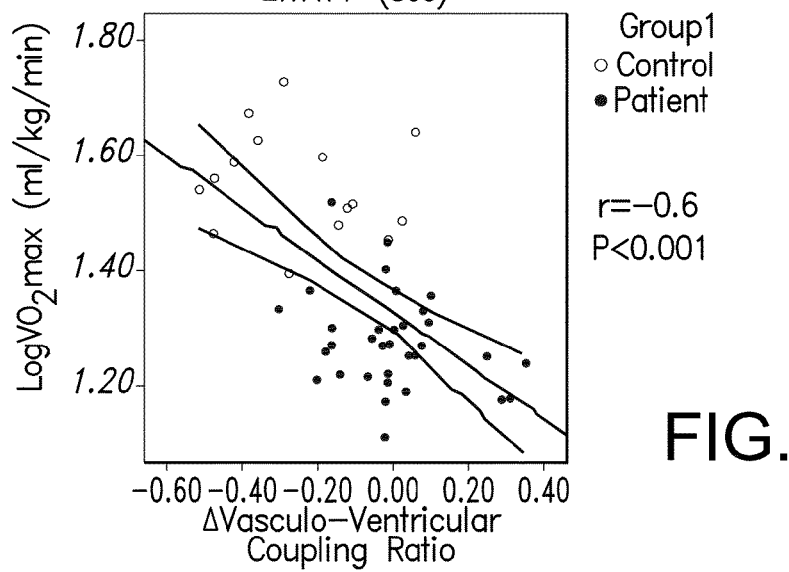
Figure 1C:
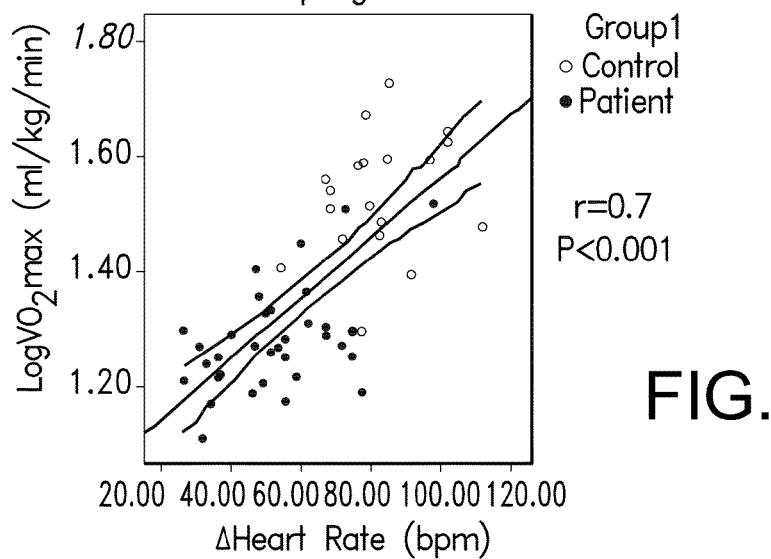

In FIGS. 1A-1C variables correlating with Aerobic Exercise Capacity ($VO_2max$) are shown. Panel A: $VO_2max$ correlated negatively with Exercise-induced Changes in nTTPF. Panel B: $VO_2max$ correlated negatively with Exercise-induced Changes in Vasculo-Ventricular Coupling Ratio. Panel C: $VO_2max$ correlated directly with Exercise-induced Changes in Heart Rate. Black circles indicate patients with HFpEF, and Open circles represents healthy controls. When patients on beta blockers were excluded from analysis, the level of significance were similar.

In FIG. 2, Panel A shows an MR images of a patient with HFpEF lying prone over a $^{31}P$ surface coil and the corresponding localized $^{31}P$ MR spectra from the left ventricle is shown in panel B. The resonances derive from PCr and the γ-, α-, and β-phosphate Resonances of the ATP. Panel C Individual PCr/γ-ATP ratio in Patients with HFpEF and Controls. The PCr/γ-ATP ratio was significantly reduced in patients with HFpEF compared to healthy controls, P=0.003

TABLE 1

Baseline Characteristics of the Subjects

| Variable | Patient (N = 37) | Control (N = 20) | P Value |
|---|---|---|---|
| Age - yr | 67 ± 9 | 63 ± 7 | 0.51 |
| Female sex - no. (%) | 28 (76) | 10 (50) | 0.05 |
| Body Mass Index | 30 ± 4 | 26 ± 5 | <0.01 |
| Left Ventricular Hypertrophy - no. (%) | 19 (51) | 5 (25) | 0.05 |
| Diabetes mellitus - no. (%) | 4 (11) | 0 | — |
| Hypertension - no. (%) | 27 (73) | 0 | — |
| Ischemic Heart Disease - no. (%) | 4 (11) | 0 | — |
| NYHA functional class - no. | | | |
| I | 10 | 0 | — |
| II | 18 | 0 | — |
| III | 8 | 0 | — |
| Drug therapy - no. (%) | | | |
| Diuretic | 10 (27) | 0 | — |
| ACE inhibitor | 20 (54) | 0 | — |
| ARB | 6 (16) | 0 | — |
| Beta-blocker | 8 (22) | 0 | — |
| Calcium blocker | 10 (27) | 0 | — |
| Alpha Blocker | 4 (11) | 0 | — |
| Spironolactone | 2 (5) | 0 | — |
| Nitrate | 3 (8) | 0 | — |
| $VO_2max$ (ml/kg/min) | 19 ± 4 | 36 ± 8 | <0.001 |
| Respiratory Exchange Ratio (RER) | 1.06 ± 0.07 | 1.13 ± 0.10 | 0.003 |
| Breathing Reserve - L/min | 36 ± 15 | 43 ± 18 | 0.16 |
| Exercise Time - min | 6 ± 2 | 7 ± 1 | 0.03 |
| Resting HR - beats/min | 74 ± 14 | 83 ± 17 | 0.03 |
| Peak HR - beats/min | 127 ± 20 | 166 ± 11 | <0.001 |
| ΔHR - beats/min | 52 ± 16 | 81 ± 14 | <0.001 |
| Rest SBP (mmHg) | 138 ± 19 | 131 ± 23 | 0.23 |
| Rest DBP (mmHg) | 81 ± 11 | 81 ± 12 | 0.98 |
| Rest MABP (mmHg) | 100 ± 12 | 96 ± 15 | 0.30 |
| Peak SBP (mm/Hg) | 182 ± 26 | 190 ± 30 | 0.30 |
| Peak DBP (mmHg) | 81 ± 13 | 84 ± 10 | 0.36 |
| Peak MABP (mmHg) | 113 ± 17 | 114 ± 25 | 0.91 |
| Left ventricular ejection fraction - % | 64 ± 14 | 63 ± 6 | 0.77 |
| Mitral E-wave velocity - m/sec | 0.72 ± 0.19 | 0.61 ± 0.12 | 0.02 |
| Mitral A-wave velocity - m/sec | 0.80 ± 0.20 | 0.59 ± 0.17 | <0.001 |
| Ratio of E-wave:A-wave velocity | 0.96 ± 0.35 | 1.03 ± 0.32 | 0.47 |
| Mitral E-wave deceleration - msec | 274 ± 70 | 269 ± 73 | 0.82 |
| E/E' (septum) | 15 ± 5 | 11 ± 3 | 0.003 |
| E/E' (lateral) | 12 ± 4 | 8 ± 2 | <0.001 |
| $E_{es}$ | 3.07 ± 1.07 | 2.60 ± .53 | 0.09 |
| $E_a$ | 2.22 ± 0.63 | 2.28 ± 0.48 | 0.69 |

Plus-minus values are means±SD. When patients on beta blockers were excluded from analysis, the level of significance were similar apart from resting HR (P=0.14). NYHA denotes New York Heart Association, ACE angiotensin-converting enzyme, ARB angiotensin II receptor blockers, BMI body mass index, SBP systolic blood pressure, DBP diastolic blood pressure, MABP mean arterial blood pressure, LA left atrium, E/E' mitral E-wave velocity-E' tissue velocity (PW-TDI) at basal inferoseptum ratio, Ees denotes Left Ventricular End-Systolic Elastance and Ea is Arterial elastance. The bodymass index is the weight in kilograms divided by the square of the height in meters.

TABLE 2

MUGA at Rest and on Exercise: Diastolic Filling Characteristics, Systolic Function, Relaxation, Stiffness, and Ventricular-Arterial Coupling

| Variable | Patient (N = 37) | Control (N = 20) | P Value |
|---|---|---|---|
| Heart Rate - rest (beats/min) | 71 ± 12 | 68 ± 15 | 0.40 |
| Heart Rate - exercise (beats/min) | 97 ± 14 | 114 ± 11 | <0.001 |
| Exercise SBP (mm/Hg) | 204 ± 26 | 198 ± 27 | 0.45 |
| Exercise DBP (mmHg) | 95 ± 15 | 97 ± 7 | 0.56 |
| Exercise MABP (mmHg) | 132 ± 15 | 131 ± 9 | 0.85 |
| Ejection fraction - rest (%) | 65 ± 9 | 64 ± 9 | 0.61 |
| Ejection fraction - exercise (%) | 66 ± 9 | 72 ± 8 | 0.05 |
| Peak emptying rates - rest (EDC/sec) | 382 ± 106 | 400 ± 90 | 0.56 |
| Peak emptying rates - exercise (EDC/sec) | 477 ± 123 | 563 ± 144 | 0.04 |
| Peak filling rates - rest (EDC/sec) | 342 ± 120 | 321 ± 111 | 0.54 |
| Peak filling rates - exercise (EDC/sec) | 504 ± 127 | 602 ± 163 | 0.02 |
| Time to peak filling - at rest (msec) | 176 ± 80 | 181 ± 56 | 0.84 |
| Time to peak filling - exercise (msec) | 246 ± 91 | 162 ± 80 | 0.001 |
| Relative Δ Stroke Volume Index | 0.99 ± 0.34 | 1.25 ± 0.47 | 0.04 |
| Relative Δ Cardiac Output Index | 1.36 ± 0.45 | 2.13 ± 0.72 | <0.001 |
| Relative Δ $E_{LV}I$ - exercise | 1.35 ± 0.50 | 1.85 ± 0.63 | 0.01 |
| Relative Δ $E_aI$ - exercise | 1.52 ± 0.48 | 1.28 ± 0.44 | 0.17 |
| Vasculo-Ventricular Coupling ratio (VVC) ($E_aI/E_{LV}I$) - rest | 0.57 ± 0.20 | 0.62 ± 0.22 | 0.36 |
| Vasculo-Ventricular Coupling ratio (VVC) ($E_aI/E_{LV}I$) - exercise | 0.55 ± 0.19 | 0.41 ± 0.15 | 0.01 |
| Δ VVC | −0.01 ± 0.15 | −0.25 ± 0.19 | <0.001 |

Plus-minus values are means±SD. When patients on beta blockers were excluded from analysis, the level of significance were similar apart from peak filling rates during exercise (P=0.08). EDC end diastolic count. SBP systolic blood pressure, DBP diastolic blood pressure, MABP mean arterial blood pressure. Relative Δ Stroke Volume Index is SVi EXERCISE/SVi REST. Relative Δ Cardiac Output Index is COi EXERCISE/COi REST. Relative Δ ELVI is ELVIEXERCISE/ELVIREST. Relative Δ EaI is EaIEXERCISE/EaIREST. Δ Vasculoventricular coupling ratio is (EaI/ELVI)EXERCISE−(EaI/ELVI)REST. Δ VVC −0.01±0.15 −0.25±0.19 <0.001.

TABLE 3

Multivariate Predictors of $VO_2$ max

| Variable | R Square | P Value |
|---|---|---|
| Exercise-induced change in HR* | 0.584 | <0.001 |
| Exercise-induced change in VVC[†] | 0.696 | 0.003 |
| Age[‡] | 0.728 | 0.018 |
| Exercise-induced change nTTPF[§] | 0.769 | 0.018 |

*Predictors: ΔHR,
[†]Predictors: ΔHR and Δ VVC coupling ratio,
[‡]Predictors: ΔHR, Δ VVC coupling ratio and age,
[§]Predictors: ΔHR, Δ VVC coupling ratio, age and ΔTTPF.
Multivariate analysis was adjusted for the variable that some patients were on betablockers.

Characteristics of the Patients

HFpEF Patients were generally females, overweight, aged 67±9 years old with a history of hypertension, however blood pressure was well treated (systolic BP 138±19 mmHg vs. 131±23 mmHg; p=0.23, in patients vs. controls) (see Table 4 below). The tissue Doppler E/E' at the basal anterolateral left ventricular wall (a measure of left ventricular end-diastolic pressure) (15), was significantly higher in patients than controls. There was also a trend (non-significant) to higher Ees in patients than in the control group. HFpEF patients also had significantly reduced $VO_2$max and reduced peak HR on metabolic exercise testing. There was a positive correlation between $VO_2$max and ΔHR (HREXERCISE−HRREST) (r=0.7, P<0.001) (see FIG. 1C). During semi-erect cycle exercise the relative stroke volume (SVi EXERCISE/SVi REST) was lower in patients compared to controls (0.99±0.34 vs. 1.25±0.47; P=0.04), and relative cardiac output (COiEXERCISE/COiREST) was also lower (1.36±0.45 vs 2.13±0.72; p<0.001). (see Table 2)

Left Ventricular Active Relaxation nTTPF is determined by the rate of active relaxation (16) and by transmitral pressure gradient at the time of mitral valve opening. nTTPF was similar at rest in HFpEF patients and controls. During exercise it shortened in controls, but lengthened in patients (Table 2). There was a negative correlation between $VO_2$max and ΔnTTPF (nTTPFEXERCISE−nTTPFREST) (r=−0.4, P=0.005) (see FIG. 1A). Furthermore, during exercise other radionuclide ventriculography diastolic filling variables such as peak filling rates as well as systolic function parameters e.g. EF and peak emptying rates, were significantly reduced in patients compared to controls. (see Table 2)

Left Ventricular Contractile Function and Vasculo-Ventricular Coupling

VVC was similar at rest in HFpEF patients and controls. During exercise, LV arterial elastance, a measure of the stiffness of the entire arterial tree, increased in both patients and controls but tended to increase more in patients. LV end systolic elastance, a measure of LV contractile function, markedly increased on exercise in controls but increased substantially less in patients. Accordingly the vasculoventricular coupling ratio was essentially unchanged on exercise inpatients but fell substantially on exercise in healthy controls furthermore whilst resting LVEF and peak emptying rate were similar in patients and controls on exercise both were lower in patients. There was a negative correlation between $VO_2$max and Δ VVC on exercise (r=−0.6, P<0.001) (FIG. 1B).

In Vivo Myocardial Energetic State

Figure 2A:
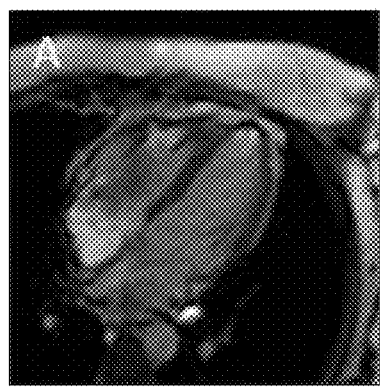
FIGS. 2A and 2B show MR images of a patient with HFpEF lying prone over a $^{31}P$ surface coil and FIG. 2C shows the corresponding localized $^{31}P$ MR spectra from the left ventricle.
Figure 2B:
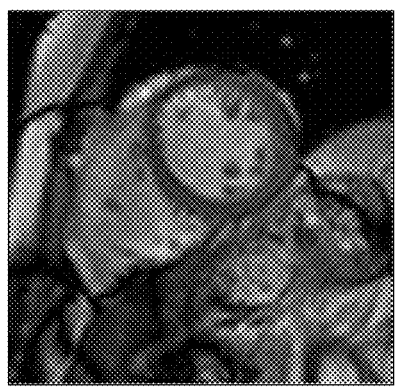
Figure 2C:
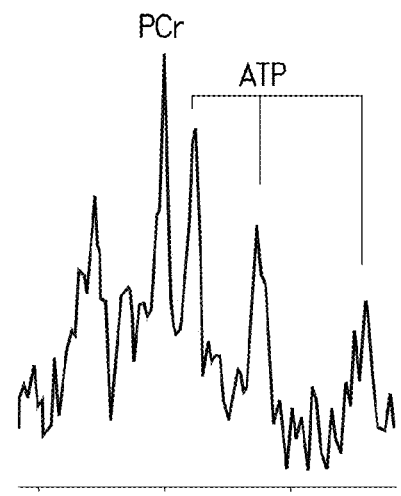
Figure 2D:
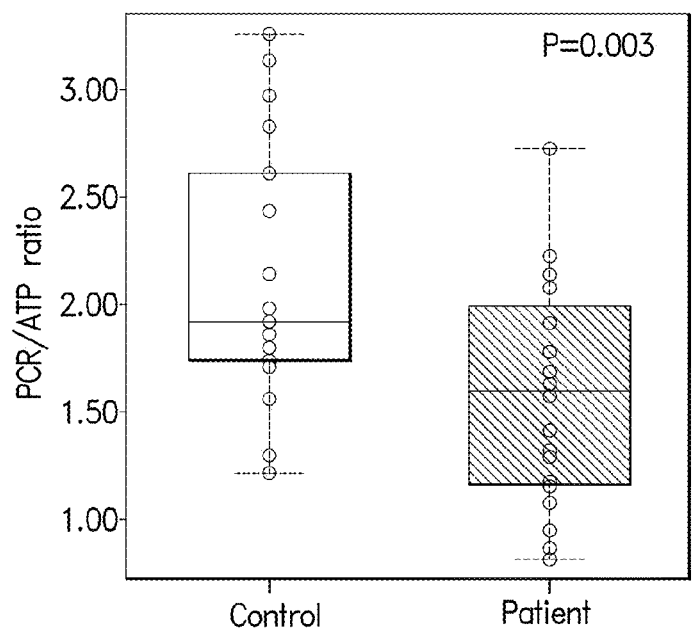
FIG. 2D is Individual PCr/γ-ATP ratio in Patients with HFpEF and Controls.

At rest, cardiac PCr/γATP ratio in HFpEF patients (N=24) was significantly reduced compared to healthy controls (N=17), 1.57±0.52 and 2.14±0.63, respectively, P=0.003 (see FIG. 2D).

Independent Predictors of Aerobic Exercise Capacity

In the multivariate analysis, a linear-regression model was used to examine $VO_2$max as the dependent variable and found that exercise-induced changes in HR, VVC and nTTPF were independent predictors of $VO_2$max. (see Table 3)

Discussion

The principal findings are: a) HFpEF patients manifest a significant reduction in PCr/γATP ratio at rest, indicating impairment of myocardial energy "reserve" that is likely to be exacerbated during exercise. b) As a corollary, during exercise, the energetically demanding active relaxation stage of diastole lengthened in patients (vs. a shortening in controls) and was accompanied with a failure to increase LV contractile function. These combined dynamic abnormalities of both diastolic and contractile function together resulted in a lower stroke volume on exercise. c) Consistent with previous studies, HFpEF patients demonstrated chronotropic incompetence on exercise. (17). d) This study underlines the importance of dynamic (rather than resting) assessment of cardiac function to comprehensively characterise patients with HFpEF.

The pathophysiology of HFpEF has been the subject of considerable controversy. These patients are typically hypertensive and exhibit impaired LV active relaxation and/or increased passive left ventricular diastolic stiffness at rest. (18) This has led many to conclude that exercise limitation is primarily a result of impaired LV diastolic filling and to the use of the term 'diastolic heart failure' by some. (19) However, diastolic dysfunction is also a common finding at rest in healthy elderly subjects. (20) Furthermore, 'subtle' abnormalities of systolic function, in particular long axis systolic function, are also almost universally observed in HFpEF patients despite normal LV ejection fraction. (21) This has led others to propose that HFpEF is predominantly a disorder of contractile function. (22) In order to compare both of these possibilities, we defined HFpEF as a limitation of exercise with an unequivocally cardiac cause as assessed by $VO_2$max (rather than using resting diastolic parameters) to avoid biasing our mechanistic studies to a select group of patients with HFpEF.

Little attention has been directed to changes in systolic and diastolic function during dynamic exercise, which is when the majority of patients experience most severe symptoms. In one study, ten patients with HFpEF were assessed with invasive pressure volume loops and compared with age-matched controls. (23) The former had increased arterial elastance (a measure of the stiffness of the entire arterial tree), and increased LV end-systolic elastance (a measure of the stiffness of the ventricle during systole, and the relatively load independent measure of the contractile state of the left ventricle. (24) Whilst diastolic abnormalities were not universally present in patients at rest, marked differences appeared during handgrip exercise. The rate of LV active relaxation increased in healthy subjects but it slowed in patients. (25) Another study from the same group, exercise-related symptoms in Afro-Caribbean hypertensive patients appeared to be strongly associated with chronotropic incompetence and an inadequate vasodilator reserve on exercise. (26)

The present study examined the patho-physiological mechanisms and predictors of exercise limitation in a substantially larger series of patients during a much more physiologically relevant form of exercise (dynamic leg exercise). There were marked dynamic abnormalities in both contractile and diastolic function of the left ventricle, and a lower peak exercise HR in patients. The independent predictors of impaired exercise capacity were abnormal ventricular-arterial coupling on exercise, a reduced HR response on exercise and a 'paradoxical' slowing of the rate of LV active relaxation on exercise (manifest as a prolongation of nTTPF). Despite the relative robustness of these observations, deciding whether these changes are adaptive or maladaptive remains challenging. The independent value of an impaired chronotropic response in predicting exercise capacity in HFpEF exemplifies this challenge. For example, $VO_2$max is largely determined by cardiac output on exercise and the latter is simply the product of HR and SV. On this basis, the detrimental consequecnes of an impaired HR appear plausible. However, in the setting of a profound slowing of active relaxation and increased LV passive diastolic stiffness, a longer diastolic filling period might be expected to be beneficial, both by increasing SV and reducing the cardiac energy load. This in part explains the efficacy of β blocker therapy in hypertrophic cardiomyopathy, a classic cause of HFpEF. (27) The latter also seems plausible, since increasing heart rate by atrial pacing has been shown to reduce supine resting stroke volume and cardiac output in patients with HFpEF. (28) Nevertheless, despite a longer diastolic filling time, the relative change in SV was lower in our patients during sub-maximal exercise. However, this failure to increase cardiac workload through limiting HR may represent a strategy of energetic parsimony in a heart with limited energy reserves. Finally, an alternative explanation is that an inadequate chronotropic response is simply a consequence and/or contributor to heart failure. (29) Such incompetence is typically present in systolic heart failure and is in part a manifestation of impaired vagal tone. (30) Clearly it will be important to undertake further studies to assess whether heart rate plays a causal role in exercise limitation in HFpEF, because if so this may be amenable to rate responsive pacing.

The same challenges arise when interpreting the role of an impairment of vasculo-ventricular coupling in HFpEF. The patients in this study had a history of hypertension but were well treated with antihypertensives (in most cases including vasodilators) therefore resting blood pressure and arterial elastance were not significantly higher than in the control group. Consistent with prior studies (31), at rest, LV end-systolic elastance (a measure of contractility or systolic stiffness) tended to be higher in patients although this did not reach significance. The increase in arterial elastance during exercise tended to be greater in patients vs. controls (presumably reflecting a greater increase in large artery stiffness). However, whilst left ventricular end-systolic elastance almost doubled during exercise in controls, the increase was only 35% in patients; hence VVC reduced by 33% during exercise in controls but was unchanged in patients. These findings indicate a blunting of the physiological increase in the contractile state of the left ventricle on exercise. As with heart rate, these changes may be interpreted to be either maladaptive or adaptive. A failure to adequately augment contractile function against a high "relative load" of disease and hence a failure to optimise cardiac energetic efficiency might be considered contributory to HFpEF. On the other hand, a smaller increment in LV end-systolic elastance will reduce the absolute increase in energy demand in an already energy constrained heart at the cost of an impaired dynamic increase in cardiac output.

Integrating these observations, we speculate that dynamic energy impairment may account for the slowing of LV active relaxation on exercise as well as the failure of LV contractile function to increase. To increase the generalisability of this hypothesis, we avoided positively biasing our study by excluding patients with established causes of cardiac energy deficiency (ischemic heart disease and diabetes) (32,33). Nevertheless, the PCr/γATP ratio was still substantially reduced in HFpEF patients vs controls at rest. The lower PCr/γATP ratio in patients indicates a reduction of high energy phosphates reserve at rest. (34,35) Although the time required for acquisition of Cardiac MRS signals precluded the measurement of high energy phosphate status on exercise, it is likely that any basal energetic impairment will be exacerbated dynamically. This exacerbation of dynamic energetic impairment would explain the prolongation of the energy demanding active relaxation as manifest by nTTPF. Moreover, the lower hearts rates and lesser increases in LV end-systolic elastance may represent strategies to limit dynamic cardiac energy demands. The cause for this resting energy deficit may relate to insulin resistance (36), to impaired mitochondrial function as a result of ageing (37), and to neuroendocrine activation and aberrant substrate metabolism. (38) Such observations provide a rationale to assess the therapeutic value of 'metabolic agents' that increase cardiac energetic status by altering cardiac substrate use (39). These agents have shown promise in patients with systolic heart failure. (40)

Study Limitations

The radionuclide exercise protocol involved asking subjects to maintain a HR which was 50% of HR reserve above their resting HR. Since this HR reserve was calibrated to peak HR rate, the absolute workload in patients was lower. To have compared patients at the same workload would be inappropriate since this would represent a higher relative workload in patients. Moreover, most changes in SV occur in the first part of exercise with subsequent increases in cardiac output being principally due to increases in HR. (41) A small proportion of patients were on β-blockers which may have affected their cardiovascular response to exercise, however, when these patients were excluded from the analysis the findings and the level of significance remained unchanged. In addition, some patients were on calcium blockers however these were all peripherally acting (dihydropyridines for hypertension) and therefore are not expected to affect the myocardium. Ideally we would have liked to measure cardiac energetics during exercise however cardiac MRS studies during exercise is currently quite challenging more so if we tried to replicate the same dynamic leg exercise in the confinement of a MR scanner. MRS and Radionuclide studies also require a regular rhythm, thus patients with atrial fibrillation were excluded from the study. In contrast, the strength of radionuclide studies is their increasing temporal resolution at higher heart rates. This obviates the confounding E:A fusion as is frequently experienced with exercise echocardiography. Radionuclide studies are thus not subject to systematically biasing mechanistic HFpEF towards a subgroup of patients without E:A fusion.

Conclusion

HFpEF patients have abnormal resting cardiac energetic status which when exacerbated dynamically may contribute to the abnormal active relaxation on exercise and to a failure to increase LV end-systolic elastance. In addition chronotropic response was markedly impaired on exercise in patients. The independent predictors of exercise capacity in patients with HFpEF are exercise-induced changes in active relaxation, heart rate and ventricular-arterial coupling.

EXAMPLE 2

A study was carried out to establish a causative role for energy deficiency and to evaluate the impact of perhexiline on cardiac energy status in HCM.

Figure 3:
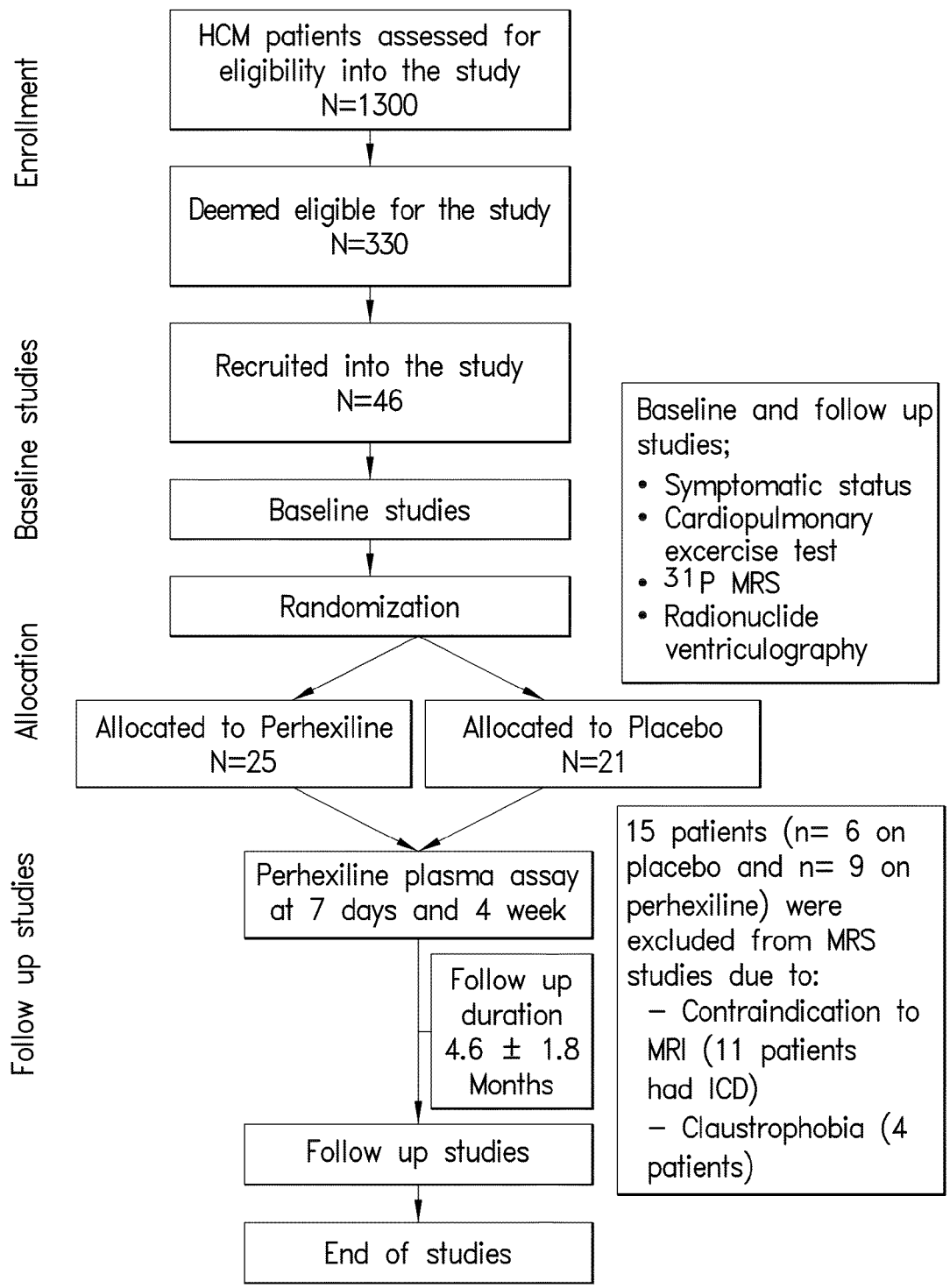
FIG. 3 is a flow chart of a study carried out to establish a causative role for energy deficiency and to evaluate the impact of perhexiline on cardiac energy status in HCM.

The study was approved by the South Birmingham Research Ethics Committee and the investigation conforms with the principles outlined in the Declaration of Helsinki. All study participants provided written informed consent. The study was a randomized, double blind, placebo-controlled parallel-group design of minimum 3 months duration. FIG. 3 represents a flow chart of the study. The pre-defined primary end point was peak oxygen consumption (peak VO2). Pre-defined secondary end points were symptomatic status, resting myocardial energetics (PCr/γ-ATP ratio) and diastolic function at rest and during exercise (nTTPF). 33 controls of similar age and gender distribution were recruited for comparison with baseline data of HCM patients. All controls had no history or symptoms of any cardiovascular disease with normal ECG and echocardiogram (LVEF≥55%).

Patients were recruited from dedicated cardiomyopathy clinics at The Heart Hospital, University College London Hospitals, London and Queen Elizabeth Hospital, Birmingham, UK between 2006 and 2008. Inclusion criteria were 18 to 80 years old symptomatic HCM patients (predominant symptom breathlessness) in sinus rhythm with reduced peak VO2 (<75% of predicted for age and gender) and no significant LVOT obstruction at rest (gradient<30 mmHg). Exclusion criteria were presence of epicardial coronary artery disease, abnormal liver function test, concomitant use of amiodarone or selective serotonin reuptake inhibitors (due to potential drug interactions with perhexiline), peripheral neuropathy and women of childbearing potential. Diabetic patients were also excluded to maintain the blindness of the study as Perhexiline may lead to a reduction in plasma glucose in such patients necessitating a reduction in anti-diabetic therapy. 46 consecutive consenting patients who met these entry criteria were recruited into the study.

Patients were subjected to a number of tests and assessments as follows.

Cardiopulmonary Exercise Test

This was performed using a Schiller CS-200 Ergo-Spiro exercise machine which was calibrated before every study. Subjects underwent spirometry and this was followed by symptom-limited erect treadmill exercise testing using a standard ramp protocol with simultaneous respiratory gas analysis (Bruce R A, McDonough J R. Stress testing in screening for cardiovascular disease. Bull N Y Acad Med 1969; 45(12):1288-1305.; Davies N J, Denison D M. The measurement of metabolic gas exchange and minute volume by mass spectrometry alone. Respir Physiol 1979; 36(2): 261-267). Peak oxygen consumption (peak VO2) was defined as the highest VO2 achieved during exercise and was expressed in ml/min/kg.

Symptomatic Status Assessment

All HCM patients filled in Minnesota Living with heart failure questionnaire and were also assessed for NHYA class.

Transthoracic Echocardiography

Echocardiography was performed with participants in the left lateral decubitus position with a Vivid 7 echocardiographic machine (GE Healthcare) and a 2.5-MHz transducer. Resting scans were acquired in standard apical 4-chamber and apical 2-chamber. LV volumes were obtained by biplane echocardiography, and LVEF was derived from a modified Simpson's formula (Lang R M, Bierig M, Devereux R B et al. Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology. J Am Soc Echocardiogr 2005; 18(12):1440-1463.) Pulse wave doppler sample volume was used to assess resting LVOTO gradient.

Radionuclide Ventriculography

Diastolic filling were assessed by equilibrium R-wave gated blood pool scintigraphy using a standard technique at rest and during graded semi erect exercise on a cycle ergometer (Atherton J J, Moore T D, Lele S S et al. Diastolic ventricular interaction in chronic heart failure. Lancet 1997; 349 (9067):1720-1724; Lele S S, Macfarlane D, Morrison S, Thomson H, Khafagi F, Frenneaux M. Determinants of exercise capacity in patients with coronary artery disease and mild to moderate systolic dysfunction. Role of heart rate and diastolic filling abnormalities. Eur Heart J 1996; 17(2): 204-212). Peak left ventricular filling rate in terms of end-diastolic count per second (EDC/s) and time to peak filling normalised for R-R interval (nTTPF) in milliseconds were measured at rest and during exercise (50% of heart rate reserve). The validity of these radionuclide measures of diastolic filling at high heart rates has been established previously (Atherton et al. and Lele et al., see above).

31P Cardiac Magnetic Resonance Spectroscopy (MRS)

Figure 4A:
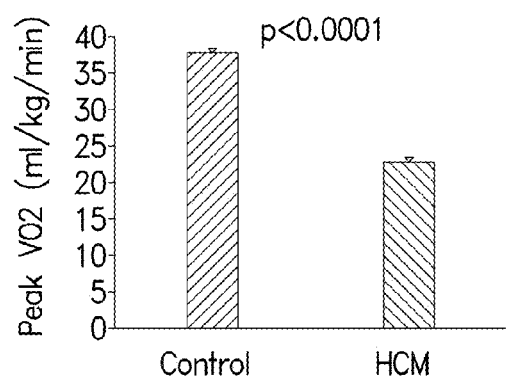
FIGS. 4A-4D represent the baseline data of HCM vs controls, more particularly.
Figure 4B:
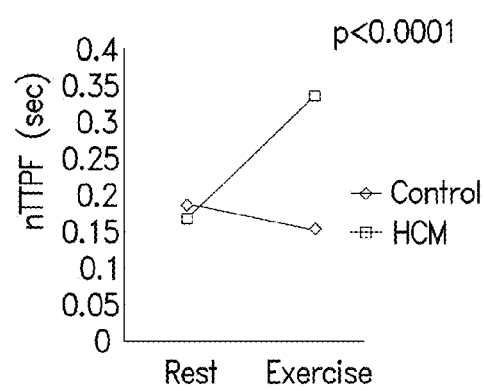
Figure 4C:
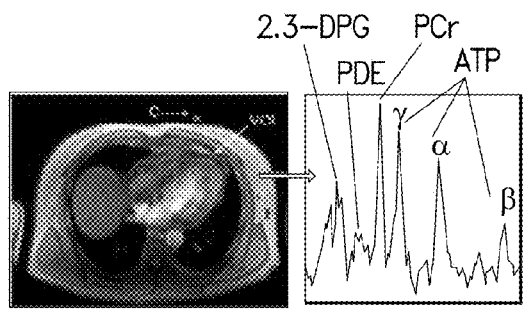

In vivo myocardial energetics were measured using a MRS at 3-Tesla Phillips Achieva 3T scanner (Shivu G N, Abozguia K, Phan T T, Ahmed I, Henning A, Frenneaux M. (31)P magnetic resonance spectroscopy to measure in vivo cardiac energetics in normal myocardium and hypertrophic cardiomyopathy: Experiences at 3T. Eur J Radiol 2008). A java magnetic resonance user interface v3.0 (jMRUI) was used for analysis (see Naressi A, Couturier C, Castang I, de Beer R, Graveron-Demilly D. Java-based graphical user interface for MRUI, a software package for quantitation of in vivo/medical magnetic resonance spectroscopy signals. Comput Biol Med 2001; 31(4):269-286)). PCr and γ-ATP peaks was used to determine the PCr/γ-ATP ratio which is a measure of the cardiac energetic state (Neubauer S, Krahe T, Schindler R et al. 31P magnetic resonance spectroscopy in dilated cardiomyopathy and coronary artery disease. Altered cardiac high-energy phosphate metabolism in heart failure. Circulation 1992; 86(6):1810-1818). Data were analyzed by an investigator who was blinded to the participants' clinical status. Carmeo-Rao ratio was used to assess signal to noise ratio. A typical example of cardiac 31P MRS spectra from a patient with HCM is shown in FIG. 4C.

adjustments were advised by an unblinded physician according to serum level to achieve therapeutic level and to avoid drug toxicity. Identical dosage adjustments were also made for randomly allocated placebo-treated patients by the unblinded observer to ensure that blinding of the investigators was maintained. At the end of study, patients were re-evaluated as described earlier.

Statistical Analysis

Data were analyzed using SPSS ver. 15.0 for Window and Microsoft Office Excel 2007, and expressed as Mean±Standard Deviation (SD). Comparison of continuous variables between Perhexiline and Placebo baseline data were determined by unpaired Student's t-test (2-tail) if variables were normally distributed and the Mann-Whitney U-test if the data were non-normally distributed. ANCOVA with baseline values as covariates was performed to test for the significance of differences in the perhexiline versus placebo group after treatment. For the primary end point, the sample size required to detect a change in peak Vo2 of 3 ml/kg/min versus placebo group with a power of 90% and probability of 5% is 44. 30 patients will be required to identify a 5 change in cardiac PCr/γATP ratio with a power of 90% and a p value of <0.05. 40 patients will be required to detect a change ≥25% in nTTPF with power of 0.99 with probability of 5%. Therefore, we aimed to study 50 patients including the drop-outs, 32 of them will take part in the MRS study.

The characteristics and treatment of participants are shown in Table 4 below. Vo$_2$: refers to peak oxygen consumption, ACE: refers to angiotensin-converting enzyme, and ARB refers to angiotensin II receptor blockers.

TABLE 4

The clinical characteristics of HCM patients and controls.

| | HCM | Controls | P value | HCM (Perhexiline) | HCM (Placebo) | P value |
|---|---|---|---|---|---|---|
| Age [years] | 55 ± 0.26 | 52 ± 0.46 | 0.2 | 56 ± 0.46 | 54 ± 0.64 | 0.42 |
| Number (Male) | 46 (34) | 33 (20) | 0.64 | 25 (19) | 21 (17) | 0.69 |
| Heart Rate [bpm] | 69 ± 0.27 | 82 ± 0.47 | <0.001* | 69 ± 0.53 | 69 ± 0.52 | 0.97 |
| Systolic BP [mm Hg] | 126 ± 0.64 | 126 ± 0.44 | 0.93 | 123 ± 0.84 | 130 ± 0.92 | 0.2 |
| Diastolic BP [mm Hg] | 76 ± 0.25 | 78 ± 0.34 | 0.33 | 74 ± 0.45 | 78 ± 0.57 | 0.24 |
| Peak Vo$_2$ [ml/kg/min] | 23 ± 0.12 | 38 ± 0.24 | <0.0001* | 22.2 ± 0.2 | 23.56 ± 0.27 | 0.42 |
| Resting nTTPF (sec) | 0.17 ± 0.002 | 0.18 ± 0.003 | 0.44 | 0.19 ± 0.003 | 0.17 ± 0.004 | 0.52 |
| PCr/γATP ratio | 1.28 ± 0.01 | 2.26 ± 0.02 | <0.0001* | 1.27 ± 0.02 | 1.29 ± 0.01 | 0.86 |
| Drug therapy - no. | | | | | | |
| Beta-blocker | 17 | 0 | — | 10 | 7 | 0.21 |
| CC-blocker | 24 | 0 | — | 11 | 8 | 0.53 |
| Diuretic | 10 | 0 | — | 4 | 5 | 0.49 |
| ACE inhibitor | 6 | 0 | — | 3 | 2 | 0.84 |
| ARB | 4 | 0 | — | 3 | 1 | 0.41 |
| Warfarin | 5 | 0 | — | 2 | 3 | 0.48 |
| Statin | 15 | 0 | — | 7 | 7 | 0.9 |

*indicates statistical significance

Intervention

Following baseline studies, patients were randomized in a double-blind fashion to receive either perhexiline (n=25) or placebo (n=21) 100 mg OD. Serum perhexiline levels were obtained at 1 and 4 weeks after initiation of the drug. Dose Baseline Data (HCM Versus Controls)

The clinical characteristics and cardiopulmonary exercise test results of all the HCM patients and controls are shown in Table 4. The groups were well matched with respect to age and gender. Heart rate was lower in the HCM group compared to controls due to medication use (beta blockers and/or calcium channel blockers).

Figure 4D:
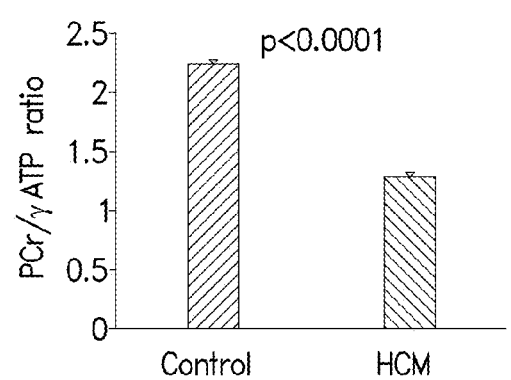

The resting cardiac PCr/γATP ratio was lower in HCM patients than in controls (1.28±0.01 vs 2.26±0.02, p<0.0001) (see FIGS. 4A and B), and this remained so after excluding patients taking beta blocker therapy (p<0.0001). At rest, nTTPF, a sensitive marker of LV relaxation, was similar in HCM patients and controls (0.17±0.002 vs 0.18±0.003 sec, p=0.44). During submaximal exercise (at a workload that achieved 50% of heart rate reserve) it remained relatively constant in controls (from 0.18±0.003 sec to 0.16±0.002 sec, [nTTPF=−0.02±0.003 sec]), but lengthened in patients (from 0.17±0.002 to 0.34±0.002 sec, [nTTPF=+0.17±0.002 sec]) p<0.0001, (FIG. 4C). This pattern persisted after exclusion of patients on beta blockers and remained significantly different from controls (p<0.0001). Patients exhibited marked exercise limitation compared to controls (23±0.12 vs 38±0.24 ml/kg/min, p<0.0001) (FIG. 4D).

Randomized, Double Blinded, Placebo-Controlled Parallel-Group

The perhexiline and placebo groups were well matched (see Table 4). Only one patient (on placebo) did not complete the study due to poor compliance. Side effects were restricted to transient nausea (n=3) and dizziness (n=2) in the perhexiline group and transient nausea (n=2) and headache (n=1) in the placebo group during the first week of treatment. There were no deaths during the study period.

Myocardial Energetics

The PCr/γATP ratio increased with perhexiline (1.27±0.02 to 1.73±0.02) as compared with placebo (1.29±0.01 to 1.23±0.01), p=0.003 (see FIG. 5A). The mean Cramer-Rao ratios for PCr and γATP were 7.5% and 10.8% respectively. The effect of perhexiline on PCr/γATP ratio remained significant after inclusion of the 3 patients with Cramer Rao ratios >20 from the analysis (p=0.02).

Diastolic Ventricular Filling

Whereas the placebo group showed similar prolongation of nTTPF during exercise before and after therapy (0.17±0.004 to 0.35±0.005 [nTTPF 0.18±0.006 sec] and 0.23±0.006 to 0.35±0.005 sec [nTTPF 0.12±0.006 sec], respectively), in the perhexiline group there was a substantial improvement on therapy with nTTPF at rest and exercise similar (0.19±0.003 to 0.19±0.004 sec [nTTPF 0.00±0.003 sec]) p=0.03 between the perhexiline and placebo response (see FIGS. 5B and 5C).

Symptomatic Status

More patients in the perhexiline group than in the placebo group had improvements in NYHA classification (67 percent vs. 30 percent) and fewer had worsening (8 percent vs. 20 percent) (p<0.001). Minnesota Living with heart failure questionnaire score showed an improvement (fall in score) in the perhexiline group (from 36.13±0.94 to 28±0.75) but did not change in the placebo group (p<0.001) (see FIGS. 5D and 5E).

Exercise Capacity (Peak Oxygen Consumption)

Peak $V_{O2}$ at baseline was similar in the perhexiline and placebo groups (Table 4). After treatment, Peak $V_{O2}$ fell by −1.23 ml/kg/min in the placebo group (from 23.56±0.27 to 22.32±0.27 ml/kg/min) but increased by 2.09 ml/kg/min in the perhexiline group (from 22.2±0.2 to 24.29±0.2 ml/kg/min), p=0.003 (see FIG. 5F).

Discussion of Results

Figure 6:
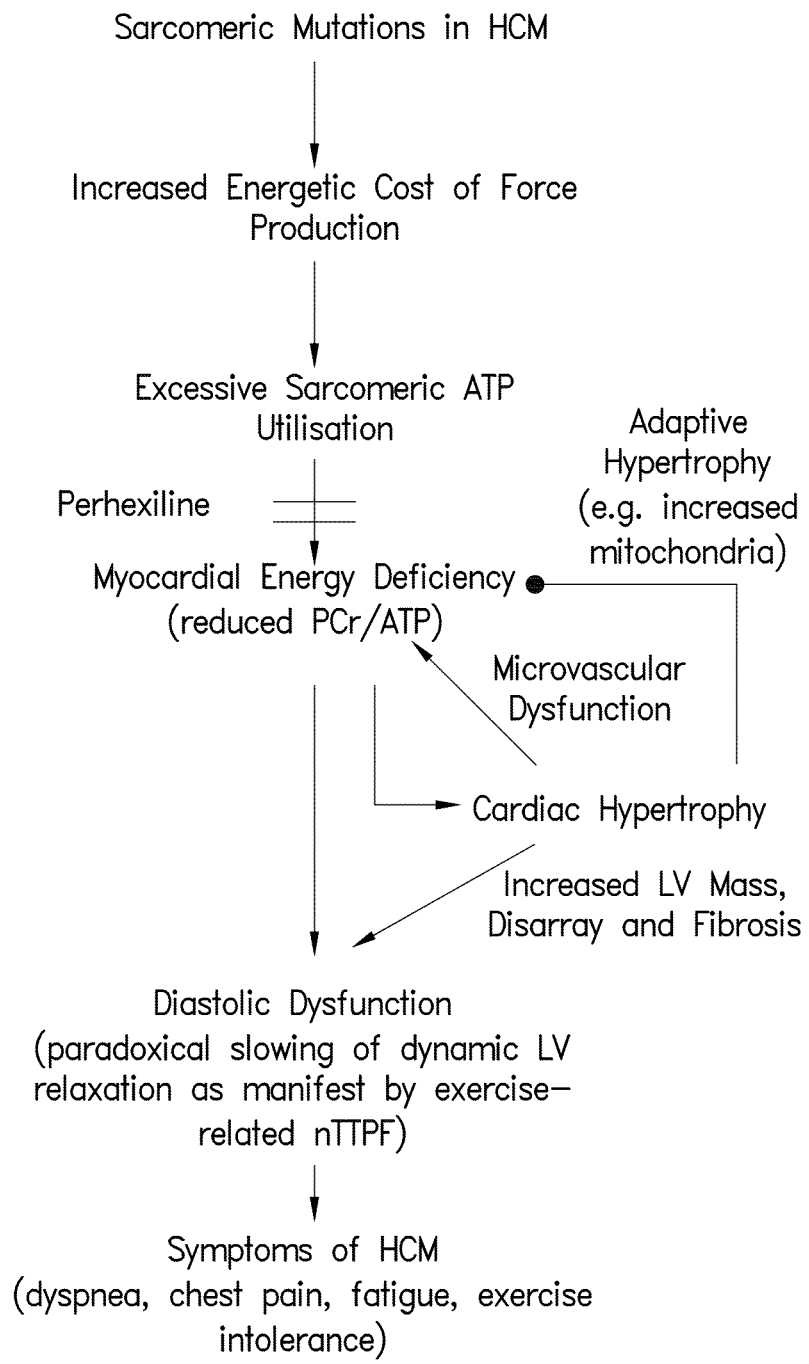
FIG. 6 illustrate the causative role for energy deficiency in the pathophysiology of HCM.

The study indicates that patients with symptomatic HCM manifest a cardiac energy defect at rest (reduced PCr/γATP ratio). This defect was accompanied by a slowing of the energy-requiring early diastolic LV active relaxation during exercise (prolongation of nTTPF). The metabolic modulator perhexiline resulted in significant myocardial energy augmentation. Supporting a causative role for energy deficiency in the pathophysiology of HCM, this energy augmentation was accompanied by striking normalisation of HCM's characteristic "paradoxical" nTTPF-prolongation in exercise. These biochemical and physiological improvements translated into significant subjective (NYHA classification and QoL score) and objective ($V_{O2}$) clinical benefits in symptomatic HCM patients already on optimal medical therapy (see FIG. 6).

The content of all cited references is expressly incorporated herein by reference for all purposes.

References

1. Hunt S A, Abraham W T, Chin M H et al. ACC/AHA 2005 Guideline Update for the Diagnosis and Management of Chronic Heart Failure in the Adult: a report of the American College of Cardiology/American Heart Association Task Force on Practice Guidelines (Writing Committee to Update the 2001 Guidelines for the Evaluation and Management of Heart Failure): developed in collaboration with the American College of Chest Physicians and the International Society for Heart and Page | 18 Lung Transplantation: endorsed by the Heart Rhythm Society. *Circulation.* 2005; 112:e154-e235.
2. Lang R M, Bierig M, Devereux R B et al. Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology. *J Am Soc Echocardiogr.* 2005; 18:1440-1463.
3. Chen C H, Fetics B, Nevo E et al. Noninvasive single-beat determination of left ventricular end-systolic elastance in humans. *J Am Coll Cardiol.* 2001; 38:2028-2034.
4. Shivu G N, Abozguia K, Phan T T, Ahmed I, Henning A, Frenneaux M. (31)P magnetic resonance spectroscopy to measure in vivo cardiac energetics in normal myocardium and hypertrophic cardiomyopathy: Experiences at 3T. Eur J Radiol 2008
5. Naressi A, Couturier C, Castang I, de Beer R, Graveron-Demilly D. Java-based graphical user interface for MRUI, a software package for quantitation of in vivo/medical magnetic resonance spectroscopy signals. Comput Biol Med 2001; 31(4):269-286.
6. Neubauer S, Krahe T, Schindler R et al. 31P magnetic resonance spectroscopy in dilated cardiomyopathy and coronary artery disease. Altered cardiac high-energy phosphate metabolism in heart failure. *Circulation.* 1992; 86:1810-1818.
7. Neubauer S, Krahe T, Schindler R et al. 31P magnetic resonance spectroscopy in dilated cardiomyopathy and coronary artery disease. Altered cardiac high-energy phosphate metabolism in heart failure. Circulation. 1992; 86:1810-1818.
8. Scheuermann-Freestone M, Madsen P L, Manners D et al. Abnormal cardiac and skeletal muscle energy metabolism in patients with type 2 diabetes. Circulation. 2003; 107: 3040-3046.
9. Lele S S, Thomson H L, Seo H et al. Exercise capacity in hypertrophic cardiomyopathy. Role of stroke volume limitation, heart rate, and diastolic filling characteristics. *Circulation.* 1995; 92:2886-2894.
10. Lele S S, Macfarlane D, Morrison S et al. Determinants of exercise capacity in patients with coronary artery disease and mild to moderate systolic dysfunction. Role of heart rate and diastolic filling abnormalities. *Eur Heart J.* 1996; 17:204-212.
11. Atherton J J, Moore T D, Lele S S et al. Diastolic ventricular interaction in chronic heart failure. *Lancet.* 1997; 349:1720-1724.
12. Bacharach S L GMBJSESE. Left ventricular peak ejection rate, filling rate and ejection fraction-frame requirements at rest and exercise: concise communication. Journal of Nuclear Medicine 20, 189-193. 1979.
13. Najjar S S, Schulman S P, Gerstenblith G et al. Age and gender affect ventricularvascular coupling during aerobic exercise. *J Am Coll Cardiol.* 2004; 44:611-617.
14. Davies N J, Denison D M. The measurement of metabolic gas exchange and minute volume by mass spectrometry alone. *Respir Physiol.* 1979; 36:261-267.
15. Ommen S R, Nishimura R A, Appleton C P et al. Clinical utility of Doppler echocardiography and tissue Doppler imaging in the estimation of left ventricular filling pressures: A comparative simultaneous Doppler-catheterization study. *Circulation.* 2000; 102:1788-1794.
16. Magorien D J, Shaffer P, Bush C et al. Hemodynamic correlates for timing intervals, ejection rate and filling rate derived from the radionuclide angiographic volume curve. *Am J Cardiol.* 1984; 53:567-571. Page | 120
17. Borlaug B A, Melenovsky V, Russell S D et al. Impaired chronotropic and vasodilator reserves limit exercise capacity in patients with heart failure and a preserved ejection fraction. *Circulation.* 2006; 114:2138-2147.
18. Zile M R, Baicu C F, Gaasch W H. Diastolic heart failure—abnormalities in active relaxation and passive stiffness of the left ventricle. N Engl J Med. 2004; 350:1953-1959.
19. Zile M R, Brutsaert D L. New concepts in diastolic dysfunction and diastolic heart failure: Part I: diagnosis, prognosis, and measurements of diastolic function. *Circulation.* 2002; 105:1387-1393.
20. Mantero A, Gentile F, Gualtierotti C et al. Left ventricular diastolic parameters in 288 normal subjects from 20 to 80 years old. *Eur Heart J.* 1995; 16:94-105.
21. Yu C M, Lin H, Yang H et al. Progression of systolic abnormalities in patients with "isolated" diastolic heart failure and diastolic dysfunction. *Circulation.* 2002; 105: 1195-1201.
22. Burkhoff D, Maurer M S, Packer M. Heart failure with a normal ejection fraction: is it really a disorder of diastolic function? *Circulation.* 2003; 107:656-658.
23. Kawaguchi M, Hay I, Fetics B et al. Combined ventricular systolic and arterial stiffening in patients with heart failure and preserved ejection fraction: implications for systolic and diastolic reserve limitations. *Circulation.* 2003; 107:714-720.
24. Grossman W, Braunwald E, Mann T et al. Contractile state of the left ventricle in man as evaluated from end-systolic pressure-volume relations. *Circulation.* 1977; 56:845-852.
25. Kawaguchi M, Hay I, Fetics B et al. Combined ventricular systolic and arterial stiffening in patients with heart failure and preserved ejection fraction: implications for systolic and diastolic reserve limitations. *Circulation.* 2003; 107:714-720.
26. Borlaug B A, Melenovsky V, Russell S D et al. Impaired chronotropic and vasodilator reserves limit exercise capacity in patients with heart failure and a preserved ejection fraction. *Circulation.* 2006; 114:2138-2147.
27. Nihoyannopoulos P, Karatasakis G, Frenneaux M et al. Diastolic function in hypertrophic cardiomyopathy: relation to exercise capacity. *J Am Coll Cardiol.* 1992; 19:536-540.
28. Westermann D, Kasner M, Steendijk P et al. Role of left ventricular stiffness in heart failure with normal ejection fraction. *Circulation.* 2008; 117:2051-2060.
29. Borlaug B A, Melenovsky V, Russell S D et al. Impaired chronotropic and vasodilator reserves limit exercise capacity in patients with heart failure and a preserved ejection fraction. *Circulation.* 2006; 114:2138-2147.
30. Eckberg D L, Drabinsky M, Braunwald E. Defective cardiac parasympathetic control in patients with heart disease. *N Engl J Med.* 1971; 285:877-883.
31. Kawaguchi M, Hay I, Fetics B et al. Combined ventricular systolic and arterial stiffening in patients with heart failure and preserved ejection fraction: implications for systolic and diastolic reserve limitations. *Circulation.* 2003; 107:714-720.
32. Neubauer S, Krahe T, Schindler R et al. 31P magnetic resonance spectroscopy in dilated cardiomyopathy and coronary artery disease. Altered cardiac high-energy phosphate metabolism in heart failure. *Circulation.* 1992; 86:1810-1818.
33. Scheuermann-Freestone M, Madsen P L, Manners D et al. Abnormal cardiac and skeletal muscle energy metabolism in patients with type 2 diabetes. *Circulation.* 2003; 107:3040-3046.
34. Lamb H J, Beyerbacht H P, van der L A et al. Diastolic dysfunction in hypertensive heart disease is associated with altered myocardial metabolism. *Circulation.* 1999; 99:2261-2267.
35. Smith C S, Bottomley P A, Schulman S P et al. Altered creatine kinase adenosine triphosphate kinetics in failing hypertrophied human myocardium. *Circulation.* 2006; 114:1151-1158.
36. Scheuermann-Freestone M NSCK. Abnormal cardiac muscle function in heart failure is related to insulin resistance. Cardiovasc J S Afr. 15, s12.
37. Szibor M, Holtz J. Mitochondrial ageing. *Basic Res Cardiol.* 2003; 98:210-218.
38. Ashrafian H, Frenneaux M P, Opie L H. Metabolic mechanisms in heart failure. *Circulation.* 2007; 116:434-448. Page | 23
39. Abozguia K, Clarke K, Lee L et al. Modification of myocardial substrate use as a therapy for heart failure. *Nat Clin Pract Cardiovasc Med.* 2006; 3:490-498.
40. Lee L, Campbell R, Scheuermann-Freestone M et al. Metabolic modulation with perhexiline in chronic heart failure: a randomized, controlled trial of short-term use of a novel treatment. *Circulation.* 2005; 112:3280-3288.
41. Higginbotham M B, Morris K G, Williams R S et al. Regulation of stroke volume during submaximal and maximal upright exercise in normal man. *Circ Res.* 1986; 58:281-291.

What is claimed is:
1. A method for treating heart failure in a mammal having a left ventricular ejection fraction of at least 50%, said method comprising administering to said mammal an effective amount of perhexiline, or a pharmaceutically acceptable salt thereof, wherein said mammal has diminished exercise capacity or tolerance.
2. The method of claim 1, wherein said mammal has a diminished peak oxygen consumption ($VO_{2max}$) during exercise (Aerobic Exercise Capacity) and wherein the effective amount of perhexiline, or a pharmaceutically acceptable salt thereof, is sufficient to increase the peak oxygen consumption ($VO_{2max}$) during exercise (Aerobic Exercise Capacity) in the mammal.

3. The method of claim 1, wherein the mammal has no significant left ventricular outflow tract obstruction at rest (gradient <30 mmHg).

4. The method of claim 1, wherein the perhexiline is in the form of a pharmaceutically acceptable salt.

5. The method of claim 4, wherein the perhexiline is in the form of a maleate salt.

6. The method of claim 1, wherein the mammal is a human.

7. The method of claim 1, further comprising co-administering to said mammal at least one additional therapeutic compound.

8. The method of claim 7, wherein the at least one additional therapeutic compound is selected from a member of the group consisting of Alpha Blockers, Beta Blockers, Calcium Channel Blockers, Diuretics, Ace (Angiotensin-Converting Enzyme) Inhibitors, Arb (Angiotensin II Receptor Blockers), Spironolactone, Nitrate, Warfarin, Verapamil, Insulin, Amiodarone, Lisinopril, Ramipril, Perindopril, Enalapril, Trandolapril, At2 Receptor Blockers, Losartan, Valsartan, Irbersartan, Carvedilol, Bisoprolol, Metoprolol, Atenolol, Aspirin, Clopidogrel, Oral Hypoglycaemics, Disopyramide, and Statins.

9. The method of claim 1, wherein the mammal is further diagnosed as having a member of the group consisting of dyspnea (shortness of breath), chest pain, fatigue, palpitation and syncope.

10. The method of claim 1, wherein the mammal is further diagnosed as having a reduced E:EA ratio, abnormally rapid skeletal muscle phosphocreatine depletion with delayed recovery, reduced systolic velocity (PSV), or no significant left ventricular outflow tract obstruction at rest (gradient <30 mmHg).

11. The method of claim 1, wherein perhexiline is administered in an amount of 300 mg per day or less.

12. The method of claim 1, wherein perhexiline is administered in an amount of 100 mg per day or less.

13. The method of claim 1, wherein perhexiline is administered in an amount of 100 mg to 300 mg per day.

* * * * *